US012570917B2

(12) United States Patent
Matsumoto

(10) Patent No.: US 12,570,917 B2
(45) Date of Patent: Mar. 10, 2026

(54) REFRIGERATOR OIL COMPOSITION AND MIXED COMPOSITION FOR REFRIGERATOR

(71) Applicant: IDEMITSU KOSAN CO., LTD., Tokyo (JP)

(72) Inventor: Tomoya Matsumoto, Funabashi (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 210 days.

(21) Appl. No.: 18/260,050

(22) PCT Filed: Mar. 10, 2022

(86) PCT No.: PCT/JP2022/010451
§ 371 (c)(1),
(2) Date: Jun. 30, 2023

(87) PCT Pub. No.: WO2022/209688
PCT Pub. Date: Oct. 6, 2022

(65) Prior Publication Data

US 2024/0309285 A1 Sep. 19, 2024

(30) Foreign Application Priority Data

Mar. 31, 2021 (JP) ................................. 2021-062425

(51) Int. Cl.

| | |
|---|---|
| ***C10M 129/74*** | (2006.01) |
| ***C07D 303/42*** | (2006.01) |
| ***C09K 5/04*** | (2006.01) |
| ***C10M 105/38*** | (2006.01) |
| ***C10M 107/24*** | (2006.01) |
| ***C10M 107/34*** | (2006.01) |
| ***C10M 129/18*** | (2006.01) |
| ***C10M 129/70*** | (2006.01) |
| ***C10M 129/72*** | (2006.01) |
| ***C10M 169/04*** | (2006.01) |
| *C10N 20/04* | (2006.01) |
| *C10N 40/30* | (2006.01) |

(52) U.S. Cl.
CPC ......... *C10M 129/74* (2013.01); *C07D 303/42* (2013.01); *C09K 5/045* (2013.01); *C10M 105/38* (2013.01); *C10M 107/24* (2013.01); *C10M 107/34* (2013.01); *C10M 129/18* (2013.01); *C10M 129/70* (2013.01); *C10M 129/72* (2013.01); *C10M 169/04* (2013.01); *C09K 2205/126* (2013.01); *C09K 2205/24* (2013.01); *C10M 2207/042* (2013.01); *C10M 2207/281* (2013.01); *C10M 2207/282* (2013.01); *C10M 2207/2835* (2013.01); *C10M 2209/043* (2013.01); *C10M 2209/1055* (2013.01); *C10N 2020/04* (2013.01); *C10N 2040/30* (2013.01)

(58) Field of Classification Search
CPC .... C09K 5/04; C09K 5/045; C09K 2205/114; C09K 2205/126; C10N 2020/02; C10N 2020/04; C10N 2020/101; C10N 2030/10; C10N 2030/08; C10N 2040/30; C10N 2030/20; C10N 2030/04
See application file for complete search history.

(56) References Cited

U.S. PATENT DOCUMENTS

| | | | |
|---|---|---|---|
| 4,248,726 | A | 2/1981 | Uchinuma et al. |
| 4,267,064 | A | 5/1981 | Sasaki et al. |
| 5,620,950 | A | 4/1997 | Kamakura et al. |
| 2004/0119047 | A1 | 6/2004 | Singh et al. |

(Continued)

FOREIGN PATENT DOCUMENTS

| | | | |
|---|---|---|---|
| CN | 104145006 | A | 11/2014 |
| CN | 104520415 | A | 4/2015 |
| CN | 106661477 | A | 5/2017 |

(Continued)

OTHER PUBLICATIONS

International Search Report issued May 24, 2022 in PCT/JP2022/010451 filed Mar. 10, 2022, 2 pages.

(Continued)

*Primary Examiner* — Vishal V Vasisth
(74) *Attorney, Agent, or Firm* — Oblon, McClelland, Maier & Neustadt, L.L.P.

(57) ABSTRACT

A refrigerator oil composition, including a refrigerant containing one or more unsaturated fluorinated hydrocarbon compounds of the following general formula (1):

$$C_xF_yH_z \quad (1)$$

where x is an integer of 2 to 6, y is an integer of 1 to 11, z is an integer of 1 to 11, and one or more carbon-carbon unsaturated bonds are present. The refrigerator oil composition further includes a base oil (A) selected from the group consisting of a polyalkylene glycol compound, a polyvinyl ether compound, a copolymer of poly(oxy)alkylene glycol or a monoether thereof and a polyvinyl ether, and a polyol ester compound, and an epoxy compound (B), where the epoxy compound (B) contains the following (B1) and (B2):

(B1) at least one divalent group represented by the following formula (1), (1)

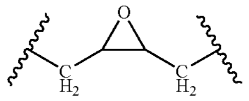

(B2) at least one ester group.

7 Claims, No Drawings

(56) References Cited

U.S. PATENT DOCUMENTS

| | | | | |
|---|---|---|---|---|
| 2015/0252281 | A1 | 9/2015 | Saito et al. | |
| 2019/0292476 | A1* | 9/2019 | Nakajima ................ | C09K 5/04 |

FOREIGN PATENT DOCUMENTS

| | | | |
|---|---|---|---|
| CN | 107250332 | A | 10/2017 |
| CN | 110494536 | A | 11/2019 |
| EP | 2 891 703 | A1 | 7/2015 |
| JP | 53-140469 | A | 12/1978 |
| JP | 55-58298 | A | 4/1980 |
| JP | 3-70796 | A | 3/1991 |
| JP | 8-226717 | A | 9/1996 |
| JP | 2006-5039651 | A | 2/2006 |
| JP | 2011-236314 | A | 11/2011 |
| JP | 2014-47267 | A | 3/2014 |

OTHER PUBLICATIONS

Written Opinion issued May 24, 2022 in PCT/JP2022/010451 (with English machine translation), 11 pages.

Japanese Office Action issued Dec. 3, 2024 in Japanese Patent Application No. 2021-062425 (with English translation), 3 pages.

Office Action issued Jul. 30, 2024, in corresponding Japanese Patent Application No. 2021-062425 (with English Translation), 6 pages.

Extended European Search Report issued Mar. 6, 2025 in European Patent Application No. 22779911.1, 9 pages.

Chinese Office Action dated Jun. 13, 2025, in Chinese Patent Application No. 202280025754.5 (with English Translation.

Official communication issued Nov. 7, 2025 in a corresponding CN application No. 202280025754.5, 30 pages (with computer-generated English translation).

* cited by examiner

REFRIGERATOR OIL COMPOSITION AND MIXED COMPOSITION FOR REFRIGERATOR

CROSS REFERENCE TO RELATED APPLICATIONS

This application is a National Stage entry under 35 U.S.C. § 371 of PCT/JP2022/010451, filed on Mar. 10, 2022, and claims priority to Japanese Patent Application No. 2021-062425, filed on Mar. 31, 2021. The entire contents of both are incorporated herein by reference.

TECHNICAL FIELD

The present invention relates to a refrigerator oil composition, and a refrigerator oil mixture composition.

In the description herein, the term "refrigerator oil mixture composition" refers to a composition obtained by mixing the "refrigerator oil composition" and the "refrigerant".

BACKGROUND ART

Refrigerators, for example, compression-type refrigerators generally include at least compressors, condensers, expansion mechanisms (for example, expansion valves and the like), and evaporators, and have a structure in which a refrigerator oil mixture composition circulates in a closed system.

As a refrigerant used in a refrigerator such as a compression-type refrigerator, a fluorinated hydrocarbon compound having a low environmental load is being used instead of a hydrochlorofluorocarbon (HCFC) which has been conventionally used in many cases. As the fluorinated hydrocarbon compounds, saturated fluorinated hydrocarbon compounds (Hydro-Fluoro-Carbon; hereinafter also referred to as "HFC") such as 1, 1,1,2-tetrafluoroethane (R134a), difluoromethane (R32), and 1,1-difluoroethane (R152a) are being used.

In addition, the use of unsaturated fluorinated hydrocarbon compounds (Hydro-Fluoro-Olefin; hereinafter also referred to as "HFO") such as 1,3,3,3-tetrafluoropropene (R1234ze), 2,3,3,3-tetrafluoropropene (R1234yf), and 1,2,3,3-tetrafluoropropene (R1234ye) having low global warming potential (GWP) has also been examined (see, for example, PTL 1).

CITATION LIST

Patent Literature

PTL 1: JP 2006-503961 T

SUMMARY OF INVENTION

Technical Problem

However, while unsaturated fluorinated hydrocarbon compounds (HFO) have an advantage of a low global warming potential (GWP), they have a disadvantage of inferior thermal stability at high temperatures compared to saturated fluorinated hydrocarbon compounds (HFC). Therefore, when the content of the unsaturated fluorinated hydrocarbon compound (HFO) in the refrigerant increases, there is a problem that the acid value of the refrigerator oil composition is likely to increase.

In addition, in recent years, refrigerators have been made more compact and higher in performance, and their operating conditions have become severer than before. Therefore, the refrigerator oil composition is required to have higher quality than ever before. For example, while the amount of refrigerator oil composition used in the equipment is decreasing along with the compactification of the refrigerator, a portion which is locally high in temperature is likely to be generated due to frictional heat and the like in the sliding portion of the compressor due to the severe operating conditions. When the refrigerator oil mixture composition is exposed to such a portion, the acid value of the refrigerator oil composition is more likely to increase.

Therefore, it is desired to create a refrigerator oil composition that can effectively suppress an increase in the acid value even when the content of the unsaturated fluorinated hydrocarbon compound (HFO) in the refrigerant is increased.

The present invention has been made in view of such a demand, and an object of the present invention is to provide a refrigerator oil composition capable of effectively suppressing an increase in an acid value even when a content of an unsaturated fluorinated hydrocarbon compound (HFO) in a refrigerant is increased, and a refrigerator oil mixture composition containing the refrigerator oil composition.

Solution to Problem

The present inventor has conducted intensive studies to solve the above problem. As a result, the present inventor has found that a refrigerator oil composition containing a specific epoxy compound can solve the above problem, and has completed the present invention.

That is, the present invention relates to the following [1] to [3].

[1] A refrigerator oil composition used for a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule], the refrigerator oil composition containing a base oil (A) selected from the group consisting of a polyalkylene glycol compound, a polyvinyl ether compound, a copolymer of poly(oxy)alkylene glycol or a monoether thereof and polyvinyl ether, and a polyol ester compound; and an epoxy compound (B), wherein the epoxy compound (B) satisfies the following requirements (B1) and (B2):

(B1) at least one divalent group represented by the following formula (1) is present in the molecule;

(1)

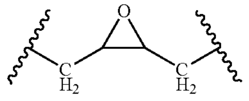

(B2) at least one ester group is present in the molecule.

[2] A refrigerator oil mixture composition containing: a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule]; and the refrigerator oil composition as set forth in [1].

[3] A method for producing a refrigerator oil composition used for a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule], the method including a step of mixing a base oil (A) selected from the group consisting of a polyalkylene glycol compound, a polyvinyl ether compound, a copolymer of poly(oxy)alkylene glycol or a monoether thereof and polyvinyl ether, and a polyol ester compound; and an epoxy compound (B), wherein the epoxy compound (B) satisfies the following requirements (B1) and (B2):

(B1) at least one divalent group represented by the following formula (1) is present in the molecule;

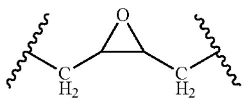

(1)

(B2) at least one ester group is present in the molecule.

Advantageous Effects of Invention

According to the present invention, it is possible to provide the refrigerator oil composition capable of effectively suppressing the increase in the acid value even when the content of an unsaturated fluorinated hydrocarbon compound (HFO) in the refrigerant is increased, and provide the refrigerator oil mixture composition containing the refrigerator oil composition.

DESCRIPTION OF EMBODIMENTS

The upper limit values and the lower limit values of the numerical ranges described herein can be arbitrarily combined. For example, when "A to B" and "C to D" are described as numerical ranges, the numerical ranges of "A to D" and "C to B" are also included in the scope of the present invention.

In addition, the numerical range "lower limit value to upper limit value" described herein means that the numerical range is equal to or higher than the lower limit value and equal to or lower than the upper limit value unless otherwise specified.

Further, in the description herein, the numerical values of the Examples are numerical values that can be used as the upper limit value or the lower limit value.

[Aspect of Refrigerator Oil Composition]

The refrigerator oil composition of the present embodiment is a refrigerator oil composition used for a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule].

The refrigerator oil composition of the present embodiment contains a base oil (A) and an epoxy compound (B). The epoxy compound (B) satisfies the following requirements (B1) and (B2):

(B1) at least one divalent group represented by the following formula (1) is present in the molecule;

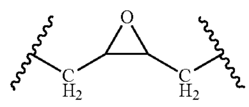

(1)

(B2) at least one ester group is present in the molecule.

The present inventor has made various studies based on the idea that one of the factors for increasing an acid value of the refrigerator oil composition with an increase in a content of an unsaturated fluorinated hydrocarbon compound (HFO) in a refrigerant is a fluorine component generated by a decomposition of the unsaturated fluorinated hydrocarbon compound (HFO) in a high-temperature environment.

As a result, it has been found that a refrigerator oil composition containing an epoxy compound (B) satisfying specific requirements can suppress an increase in the fluorine concentration in the refrigerator oil composition resulting from the fluorine component generated by a decomposition of the unsaturated fluorinated hydrocarbon compound (HFO) in a high-temperature environment, thereby suppressing an increase in the acid value of the refrigerator oil composition.

The mechanism by which the effects of the present invention are exhibited is presumed as follows.

That is, as compared with an epoxy compound having a structure having an epoxy group at a molecular terminal, the epoxy compound (B) having an epoxy group inside the molecule is less likely to decompose an unsaturated fluorinated hydrocarbon compound (HFO). Therefore, it is difficult to generate a fluorine component (for example, hydrofluoric acid) generated by the decomposition of the unsaturated fluorinated hydrocarbon compound (HFO) particularly in a high-temperature environment, and a small amount of the generated fluorine component reacts with the epoxy group in the epoxy compound (B) and is captured in the epoxy compound (B).

That is, it is presumed that the use of the epoxy compound (B) makes it difficult to decompose HFO, and as a result, the elution of the fluorine component into the refrigerator oil composition is suppressed and the eluted fluorine component can be captured, so that the increase in the acid value of the refrigerator oil composition can be suppressed.

In the following description, "base oil (A)" and "epoxy compound (B)" are also referred to as "component (A)" and "component (B)", respectively.

The refrigerator oil composition of the present embodiment may be composed of only the component (A) and the component (B), but may contain other components in addition to the component (A) and the component (B) as long as the effects of the present invention are not impaired.

In the refrigerator oil composition of the present embodiment, the total content of the component (A) and the component (B) is preferably 80% by mass to 100% by mass, more preferably 85% by mass to 100% by mass, and still more preferably 90% by mass to 100% by mass based on the total amount (100% by mass) of the refrigerator oil composition.

Hereinafter, each of the components contained in the refrigerator oil composition of the present embodiment will be described in detail.

<Base Oil (A)>

The refrigerator oil composition of the present embodiment contains the base oil (A).

In the refrigerator oil composition of the present embodiment, the content of the base oil (A) is preferably 85.0% by mass or more, more preferably 90.0% by mass or more, and still more preferably 92.0% by mass or more, based on the total amount (100% by mass) of the refrigerator oil composition, from the viewpoint of long-term stability required for the refrigerator oil composition. On the other hand, the content of the base oil (A) is preferably 99.0% by mass or less, more preferably 98.5% by mass or less, and still more preferably 98.0% by mass or less, from the viewpoint of easily ensuring the content of the epoxy compound (B) in the refrigerator oil composition and further from the viewpoint of easily ensuring the content of additives other than the epoxy compound (B).

The upper limit values and the lower limit values of these numerical ranges can be arbitrarily combined. Specifically, it is preferably 85.0% by mass to 99.0% by mass, more preferably 90.0% by mass to 98.5% by mass, and still more preferably 92.0% by mass to 98.0% by mass.

As the base oil (A), any base oil commonly used in refrigerator oil composition can be used without particular limitation. For example, as the base oil (A), one or more selected from the group consisting of synthetic oils and mineral oils can be used.

Here, in the refrigerator oil composition of the present embodiment, the base oil (A) is preferably a synthetic oil from the viewpoint of solubility of the epoxy compound (B).

Among synthetic oils, the base oil (A) preferably contains one or more base oils (hereinafter also referred to as "base oil (A1)") selected from the group consisting of a polyalkylene glycol compound (hereinafter also referred to as "PAG"), a polyvinyl ether compound (hereinafter also referred to as "PVE"), a copolymer of poly(oxy)alkylene glycol or a monoether thereof and polyvinyl ether (hereinafter also referred to as "ECP"), and a polyol ester compound (hereinafter also referred to as "POE"), from the viewpoint of improving the thermal stability of the refrigerator oil composition.

Further, from the viewpoints of improving compatibility with a refrigerant, improving hydrolysis resistance, and further improving thermal stability of the refrigerator oil composition, it is more preferable that the base oil (A) contains one or more base oils selected from the group consisting of PAG and PVE (hereinafter also referred to as "base oil (A2)").

PAG, PVE, ECP, and POE will be described in detail below.

(Polyalkylene Glycol Compound (PAG))

As PAG, a PAG used as a base oil in a refrigerator oil composition can be used without particular limitation, but a polymer (A-1) represented by the following general formula (A-1) is preferable.

$$R^{13a}—[(OR^{14a})_p—OR^{15a}]_q \qquad (A\text{-}1)$$

When the base oil (A) contains PAG, one kind of PAG may be used alone, or two or more kinds of PAG may be used in combination.

In the general formula (A-1), $R^{13a}$ represents a hydrogen atom, a monovalent hydrocarbon group having 1 to 10 carbon atoms, an acyl group having 2 to 10 carbon atoms, a divalent to hexavalent hydrocarbon group having 1 to 10 carbon atoms, or a substituted or unsubstituted heterocyclic group having 3 to 10 ring atoms; $R^{14a}$ represents an alkylene group having 2 to 4 carbon atoms; and R15a represents a hydrogen atom, a monovalent hydrocarbon group having 1 to 10 carbon atoms, an acyl group having 2 to 10 carbon atoms, or a substituted or unsubstituted heterocyclic group having 3 to 10 ring atoms.

Examples of the substituent which the heterocyclic group may have include an alkyl group having 1 to 10 (preferably 1 to 6, and more preferably 1 to 3) carbon atoms: a cycloalkyl group having 3 to 10 (preferably 3 to 8, and more preferably 5 or 6) ring carbon atoms; an aryl group having 6 to 18 (preferably 6 to 12) ring carbon atoms; a halogen atom (fluorine atom, chlorine atom, bromine atom, iodine atom); a cyano group; a nitro group; a hydroxy group; and an amino group.

These substituents may be further substituted with the above-mentioned optional substituents.

q is an integer of 1 to 6, preferably an integer of 1 to 3, and more preferably 1.

q is determined in accordance with the number of bonding sites of the R13a in the general formula (A-1). For example, when $R^{13a}$ is an alkyl group or an acyl group, q becomes 1, and when $R^{13a}$ is a hydrocarbon group or a heterocyclic group and the valence of the group is 2, 3, 4, 5, or 6, q becomes 2, 3, 4, 5, or 6, respectively.

p is a number of the repeating unit of $OR^{14a}$, and is usually 1 or more, and preferably a number such that p×q is 6 to 80. The value of p is a value that is appropriately set to adjust the 40° C. kinematic viscosity of the base oil (A) to an appropriate range, and is not particularly limited as long as the 40° C. kinematic viscosity is adjusted to an appropriate range.

Note that the plurality of R14a's may be the same or different from each other. When q is 2 or more, a plurality of R15a's in one molecule may be the same or different from each other.

Examples of the monovalent hydrocarbon group represented by $R^{13a}$ and $R^{15a}$ include alkyl groups such as a methyl group, an ethyl group, a n-propyl group, an isopropyl group, various butyl groups, various pentyl groups, various hexyl groups, various heptyl groups, various octyl groups, various nonyl groups, and various decyl groups; cycloalkyl groups such as a cyclopentyl group, a cyclohexyl group, various methylcyclohexyl groups, various ethylcyclohexyl groups, various propylcyclohexyl groups, and various dimethylcyclohexyl groups; aryl groups such as a phenyl group, various methylphenyl groups, various ethylphenyl groups, various dimethylphenyl groups, various propylphenyl groups, various trimethylphenyl groups, various butylphenyl groups, and various naphthyl groups; and arylalkyl groups such as a benzyl group, various phenylethyl groups, various methylbenzyl groups, various phenylpropyl groups, and various phenylbutyl groups. The alkyl group may be either linear or branched.

Here, "various" represents a "linear, branched, or cyclic" hydrocarbon group. For example, "various butyl groups" represent various butyl groups such as "a n-butyl group, a sec-butyl group, an isobutyl group, a tert-butyl group, and a cyclobutyl group". A group having a cyclic structure includes positional isomers such as an ortho isomer, a meta isomer, and a para isomer, and the same applies hereinafter.

The number of carbon atoms of the monovalent hydrocarbon group represented by $R^{13a}$ and $R^{15a}$ is preferably 1 to 10, more preferably 1 to 6, and still more preferably 1 to 3, from the viewpoint of the compatibility with a refrigerant.

The hydrocarbon group moiety of the acyl groups having 2 to 10 carbon atoms represented by $R^{13a}$ and $R^{15a}$ may be linear, branched, or cyclic. Examples of the alkyl group moiety include those having 1 to 9 carbon atoms among the hydrocarbon groups represented by $R^{13a}$ and $R^{15a}$ described above.

The number of carbon atoms of the acyl group represented by $R^{13a}$ and R15a is preferably 2 to 8, and more preferably 2 to 6, from the viewpoint of the compatibility with a refrigerant.

Examples of the divalent to hexavalent hydrocarbon group represented by $R^{13a}$ include residual groups obtained by further removing 1 to 5 hydrogen atoms from the monovalent hydrocarbon group represented by R13a, residual groups obtained by removing a hydroxy group from a polyhydric alcohol such as trimethylolpropane, glycerin, pentaerythriol, sorbitol, 1,2,3-trihydroxycyclohexane, or 1,3,5-trihydroxycyclohexane.

The number of carbon atoms of the divalent to hexavalent acyl group represented by $R^{13a}$ is preferably 2 to 10, and more preferably 2 to 6, from the viewpoint of the compatibility with a refrigerant.

The heterocyclic group represented by $R^{13a}$ and $R^{15a}$ is preferably an oxygen atom-containing heterocyclic group or a sulfur atom-containing heterocyclic group. In addition, the heterocyclic group may be a saturated ring or an unsaturated ring.

Examples of the oxygen atom-containing heterocyclic group include residual groups obtained by removing 1 to 6 hydrogen atoms contained in an oxygen atom-containing saturated heterocyclic ring such as ethylene oxide, 1,3-propylene oxide, tetrahydrofuran, tetrahydropyran, and hexamethylene oxide or an oxygen atom-containing unsaturated heterocyclic ring such as acetylene oxide, furan, pyran, oxycycloheptatriene, isobenzofuran, and isochromene.

Further, examples of the sulfur atom-containing heterocyclic group include residual groups obtained by removing 1 to 6 hydrogen atoms contained in a sulfur atom-containing saturated heterocyclic ring such as ethylene sulfide, trimethylene sulfide, tetrahydrothiophene, tetrahydrothiopyran, and hexamethylene sulfide or a sulfur atom-containing unsaturated heterocyclic ring such as acetylene sulfide, thiophene, thiapyran, and thiotripylidene.

The heterocyclic groups represented by $R^{13a}$ and $R^{15a}$ may have a substituent, and the substituent may be bonded to the oxygen atom in the general formula (A-1). The substituent is as described above, and is preferably an alkyl group having 1 to 6 carbon atoms, and more preferably an alkyl group having 1 to 3 carbon atoms.

The number of ring atoms of the heterocyclic group is preferably 3 to 10, and more preferably 3 to 6, from the viewpoint of the compatibility with a refrigerant.

Examples of the alkylene group represented by $R^{14a}$ include alkylene groups having 2 carbon atoms such as a dimethylene group ($-CH_2CH_2-$) and an ethylene group ($-CH(CH_3)-$); alkylene groups having 3 carbon atoms such as a trimethylene group ($-CH_2CH_2CH_2-$), a propylene group ($-CH(CH_3)CH_2-$), a propylidene group ($-CHCH_2CH_3-$), and an isopropylidene group ($-C(CH_3)_2-$); and alkylene groups having 4 carbon atoms such as a tetramethylene group ($-CH_2CH_2CH_2CH_2-$), a 1-methyltrimethylene group ($-CH(CH_3)CH_2CH_2-$), a 2-methyltrimethylene group ($-CH_2CH(CH_3)CH_2-$), and a butylene group ($-C(CH_3)_2CH_2-$). Among them, a propylene group ($-CH(CH_3)CH_2-$) is preferable as $R^{14a}$.

In the polymer (A-1) represented by the general formula (A-1), the content of the oxypropylene unit ($-OCH(CH_3)CH_2-$) is preferably 50 mol % or more, more preferably 65 mol % or more, and still more preferably 80 mol % or more based on the total amount (100 mol %) of oxyalkylene ($OR^{14a}$) in the polymer (A-1).

Among the polymers (A-1) represented by the general formula (A-1), at least one kind selected from the group consisting of polyoxypropylene glycol dimethyl ether represented by the following general formula (A-1-i), polyoxyethylene polyoxypropylene glycol dimethyl ether represented by the following general formula (A-1-ii), polyoxypropylene glycol monobutyl ether represented by the following general formula (A-1-iii), polyoxypropylene glycol monomethyl ether represented by the following general formula (A-1-iv), and polyoxypropylene glycol diacetate is preferable.

(A-1-i)

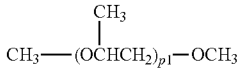

(In the formula (A-1-i), p1 represents a number of 1 or more, and preferably a number of 6 to 80.)

(A-1-ii)

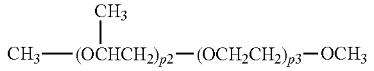

(In the formula (A-1-ii), p2 and p3 each independently represent a number of 1 or more, and preferably a number such that the value of p2+p3 is 6 to 80.)

(A-1-iii)

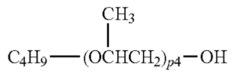

(In the formula (A-1-iii), p4 represents a number of 1 or more, and preferably a number of 6 to 80.)

(A-1-iv)

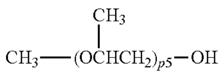

(In the formula (A-1-iv), p5 represents a number of 1 or more, and preferably a number of 6 to 80.)

p1 in the general formula (a-1-i), p2 and p3 in the general formula (a-1-ii), p4 in the general formula (a-1-iii), and p5 in the general formula (a-1-iv) may be appropriately selected depending on the kinematic viscosity required for the base oil (A).

(Polyvinyl Ether Compound (PVE))

PVE is a polymer having one or more kinds of a structural unit derived from vinyl ether, and PVE used as a base oil in refrigerator oil composition can be used without any particular limitation.

When the base oil (A) contains PVE, one kind of PVE may be used alone, or two or more kinds of PVE may be used in combination.

From the viewpoint of the compatibility with a refrigerant, PVE is preferably a polymer having one or more kinds of a structural unit derived from vinyl ether and having an alkyl group having 1 to 4 carbon atoms in a side chain. From the viewpoint of further improving the compatibility with a refrigerant, the alkyl group is preferably a methyl group or an ethyl group, and more preferably a methyl group.

PVE is preferably a polymer (A-2) having one or more kinds of a structural unit represented by the following general formula (A-2).

(A-2)

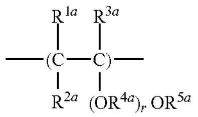

In the formula (A-2), $R^{1a}$, $R^{2a}$, and $R^{3a}$ each independently represent a hydrogen atom or a hydrocarbon group having 1 to 8 carbon atoms. R4a represents a divalent hydrocarbon group having 2 to 10 carbon atoms. R5a represents a hydrocarbon group having 1 to 10 carbon atoms. r is a number of the repeating unit of $OR^{4a}$, and is usually 0 to 10, preferably 0 to 5, more preferably 0 to 3, and still more preferably 0. When a plurality of $OR^{4a}$'s are present in the structural unit represented by the general formula (A-2), the plurality of $OR^{4a}$'s may be identical to or different from each other.

Examples of the hydrocarbon group having 1 to 8 carbon atoms represented by $R^{1a}$, $R^{2a}$ and $R^{3a}$ include alkyl groups such as a methyl group, an ethyl group, a n-propyl group, an isopropyl group, various butyl groups, various pentyl groups, various hexyl groups, various heptyl groups, and various octyl groups; cycloalkyl groups such as a cyclopentyl group, a cyclohexyl group, various methylcyclohexyl groups, various ethylcyclohexyl groups, and various dimethylcyclohexyl groups; aryl groups such as a phenyl group, various methylphenyl groups, various ethylphenyl groups, and various dimethylphenyl groups; and arylalkyl groups such as a benzyl group, various phenylethyl groups, and various methylbenzyl groups.

The number of carbon atoms of the hydrocarbon group represented by $R^{1a}$, $R^{2a}$, and $R^{3a}$ is preferably 1 to 6, and more preferably 1 to 3.

$R^{1a}$, $R^{2a}$, and $R^{3a}$ are each independently preferably a hydrogen atom or an alkyl group having 1 to 8 carbon atoms, more preferably a hydrogen atom or an alkyl group having 1 to 3 carbon atoms, and still more preferably a hydrogen atom.

Examples of the divalent hydrocarbon group having 2 to 10 carbon atoms represented by $R^{4a}$ include divalent aliphatic groups such as an ethylene group, a 1,2-propylene group, a 1,3-propylene group, various butylene groups, various pentylene groups, various hexylene groups, various heptylene groups, various octylene groups, various nonylene groups, and various decylene groups; divalent alicyclic groups such as cyclohexane, methylcyclohexane, ethylcyclohexane, dimethylcyclohexane, and propylcyclohexane; divalent aromatic groups such as various phenylene groups, various methylphenylene groups, various ethylphenylene groups, various dimethylphenylene groups, and various naphthylene groups; divalent alkylaromatic groups having a monovalent bonding site each on the alkyl group moiety and the aromatic moiety of alkylaromatic hydrocarbons such as toluene, xylene, and ethylbenzene; and divalent alkylaromatic groups having bonding sites on the alkyl group moiety of polyalkylaromatic hydrocarbons such as xylene and diethylbenzene.

The number of carbon atoms of the hydrocarbon group represented by $R^{4a}$ is preferably 2 to 6, and more preferably 2 to 4.

$R^{4a}$ is preferably a divalent aliphatic group having 2 to 10 carbon atoms, and more preferably a divalent aliphatic group having 2 to 4 carbon atoms.

Examples of the hydrocarbon group having 1 to 10 carbon atoms represented by $R^{5a}$ include alkyl groups such as a methyl group, an ethyl group, a n-propyl group, an isopropyl group, various butyl groups, various pentyl groups, various hexyl groups, various heptyl groups, various octyl groups, various nonyl groups, and various decyl groups; cycloalkyl groups such as a cyclopentyl group, a cyclohexyl group, various methylcyclohexyl groups, various ethylcyclohexyl groups, various propylcyclohexyl groups, and various dimethylcyclohexyl groups: aryl groups such as a phenyl group, various methylphenyl groups, various ethylphenyl groups, various dimethylphenyl groups, various propylphenyl groups, various trimethylphenyl groups, various butylphenyl groups, and various naphthyl groups; and arylalkyl groups such as a benzyl group, various phenylethyl groups, various methylbenzyl groups, various phenylpropyl groups, and various phenylbutyl groups.

The number of carbon atoms of the hydrocarbon group represented by $R^{5a}$ is preferably 1 to 8, and more preferably 1 to 6.

$R^{5a}$ is preferably an alkyl group having 1 to 6 carbon atoms, more preferably an alkyl group having 1 to 4 carbon atoms, still more preferably a methyl group or an ethyl group, and even more preferably a methyl group, from the viewpoint of further improving the compatibility with a refrigerant.

The number of units (degree of polymerization) of the structural unit represented by the general formula (A-2) is appropriately selected according to the kinematic viscosity required for the base oil (A).

The polymer having the structural unit represented by the general formula (A-2) may be a homopolymer having only one kind of the structural unit or a copolymer having two or more kinds of the structural units. When the polymer is a copolymer, the form of copolymerization is not particularly limited and may be any of a block copolymer, a random copolymer, and a graft copolymer.

A monovalent group derived from a saturated hydrocarbon, ether, alcohol, ketone, amide, nitrile or the like may be introduced into the terminal portion of the polymer (A-2). Among these, in the polymer (A-2), one terminal portion is preferably a group represented by the following general formula (A-2-i).

(A-2-i)

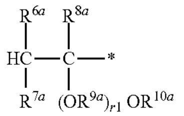

In the formula (A-2-i), * represents a bonding position to a carbon atom in the structural unit represented by the general formula (A-2).

In the formula (A-2-i), $R^{6a}$, $R^{7a}$, and $R^{8a}$ each independently represent a hydrogen atom or a hydrocarbon group having 1 to 8 carbon atoms, preferably a hydrogen atom or a hydrocarbon group having 1 to 6 carbon atoms, and more preferably a hydrogen atom or an alkyl group having 1 to 3 carbon atoms.

Examples of the hydrocarbon group having 1 to 8 carbon atoms represented by $R^{6a}$, $R^{7a}$, and $R^{8a}$ include the same groups as those exemplified as the hydrocarbon group having 1 to 8 carbon atoms represented by $R^{1a}$, $R^{2a}$, and $R^{3a}$ in the general formula (A-2).

In the formula (A-2-i), $R^{9a}$ represents a divalent hydrocarbon group having 2 to 10 carbon atoms, preferably a divalent hydrocarbon group having 2 to 6 carbon atoms, and more preferably a divalent aliphatic group having 2 to 4 carbon atoms.

In the formula (A-2-i), r1 is a number of the repeating unit of $OR^{9a}$, and is usually 0 to 10, preferably 0 to 5, more preferably 0 to 3, and still more preferably 0. When a plurality of $OR^{9a}$'s are present in the structural unit represented by the general formula (A-2-i), the plurality of $OR^{9a}$'s may be identical to or different from each other.

Examples of the divalent hydrocarbon group having 2 to 10 carbon atoms represented by $R^{9a}$ include the same groups as those exemplified as the divalent hydrocarbon group having 2 to 10 carbon atoms represented by $R^{4a}$ in the general formula (A-2).

In the formula (A-2-i), $R^{10a}$ represents a hydrocarbon group having 1 to 10 carbon atoms, preferably a hydrocarbon group having 1 to 8 carbon atoms, and more preferably an alkyl group having 1 to 8 carbon atoms.

As $R^{10a}$, an alkyl group having 1 to 6 carbon atoms is preferable when r1 in the general formula (A-2-i) is 0, and an alkyl group having 1 to 4 carbon atoms is preferable when r1 is 1 or more.

Examples of the hydrocarbon group having 1 to 10 carbon atoms represented by $R^{10a}$ include the same groups as those exemplified as the hydrocarbon group having 1 to 10 carbon atoms represented by $R^{5a}$ in the general formula (A-2).

In the polymer (A-2), when one terminal portion is a group represented by the general formula (A-2-i), the other terminal portion is preferably any one of a group represented by the general formula (A-2-i), a group represented by the following general formula (A-2-ii), a group represented by the following general formula (A-2-iii), and a group having an olefinic unsaturated bond.

(A-2-ii)

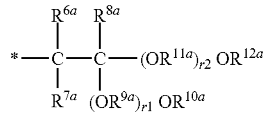

(A-2-iii)

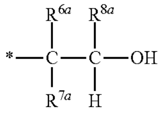

In the formulae (A-2-ii) and (A-2-iii), $R^{6a}$, $R^{7a}$, $R^{8a}$, $R^{9a}$, $R^{10a}$, and r1 are the same as defined in the general formula (A-2-i). In addition, in the formula (A-2-ii), $R^{11a}$, $R^{12a}$, and r2 are the same as the definitions of $R^{9a}$, $R^{10a}$, and r1 in the general formula (A-2-i), respectively.

(Copolymer of poly(oxy)alkylene glycol or monoether thereof and polyvinyl ether (ECP))

The copolymer (ECP) of poly(oxy)alkylene glycol or a monoether thereof and polyvinyl ether may be a copolymer having a structural unit derived from poly(oxy)alkylene glycol or a monoether thereof and a structural unit derived from polyvinyl ether.

The term "poly(oxy)alkylene glycol" refers to both polyalkylene glycol and polyoxyalkylene glycol.

When the base oil (A) contains ECP, one kind of ECP may be used alone, or two or more kinds of ECP may be used in combination.

Among the ECP's, a copolymer (A-3-i) represented by the following general formula (A-3-i) or a copolymer (A-3-ii) represented by the following general formula (A-3-ii) is preferable.

(A-3-i)

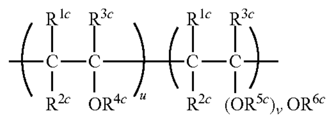

(A-3-ii)

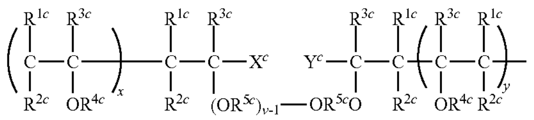

In the general formulae (A-3-i) and (A-3-ii), $R^{1c}$, $R^{2c}$, and $R^{3c}$ each independently represent a hydrogen atom or a hydrocarbon group having 1 to 8 carbon atoms.

$R^{4c}$ each independently represents a hydrocarbon group having 1 to 10 carbon atoms.

$R^{5c}$ each independently represents an alkylene group having 2 to 4 carbon atoms.

$R^{6c}$ each independently represents a hydrogen atom, an alkyl group having 1 to 20 carbon atoms, a substituted or unsubstituted alicyclic group having 3 to 20 ring carbon atoms, a substituted or unsubstituted aromatic group having 6 to 24 ring carbon atoms, an acyl group having 2 to 20 carbon atoms, or an oxygen-containing hydrocarbon group having 2 to 50 carbon atoms.

When a plurality of $R^{1c}$'s, $R^{2c}$'s, $R^{3c}$'s, $R^{4c}$'s, $R^{5c}$'s, and $R^{6c}$'s are present, they may be the same or different for each structural unit.

$X^C$ and $Y^C$ each independently represent a hydrogen atom, a hydroxy group, or a hydrocarbon group having 1 to 20 carbon atoms.

v in the general formulae (A-3-i) and (A-3-ii) represents an average value of the number of the unit represented by $OR^{5c}$, and represents a number of 1 or more, and preferably a number of 1 to 50. When a plurality of $OR^{5c}$'s are present, the plurality of $OR^{5c}$'s may be the same or different. In addition, "$OR^{5c}$" represents a structural unit derived from poly(oxy)alkylene glycol or a monoether thereof.

u in the general formula (A-3-i) represents a number of 0 or more and is preferably a number of 0 to 50, and w represents a number of 1 or more and is preferably a number of 1 to 50.

x and y in the general formula (A-3-ii) each independently represent a number of 1 or more, and preferably a number of 1 to 50.

The values of v, u, w, x, and y are not particularly limited as long as they are adjusted according to the hydroxyl value required for the base oil (A).

The form of copolymerization of the copolymer (A-3-i) and the copolymer (A-3-ii) is not particularly limited, and may be a block copolymer, a random copolymer, or a graft copolymer.

Examples of the hydrocarbon group having 1 to 8 carbon atoms that may be selected as $R^{1c}$, $R^{2c}$, and $R^{3c}$ include the same monovalent hydrocarbon group having 1 to 8 carbon atoms that may be selected as $R^{1a}$, $R^{2a}$, and $R^{3a}$ in the general formula (A-1).

The number of carbon atoms of the hydrocarbon group that may be selected as $R^{1c}$, $R^{2c}$, and $R^{3c}$ is preferably 1 to 8, more preferably 1 to 6, and still more preferably 1 to 3.

$R^{1c}$, $R^{2c}$, and $R^{3c}$ are each independently preferably a hydrogen atom or an alkyl group having 1 to 8 carbon atoms, more preferably a hydrogen atom or an alkyl group having 1 to 6 carbon atoms, and still more preferably a hydrogen atom or an alkyl group having 1 to 3 carbon atoms.

In addition, it is preferable that at least one of $R^{1c}$, $R^{2c}$, and $R^{3c}$ is a hydrogen atom, and it is more preferable that all of $R^{1c}$, $R^{2c}$, and $R^{3c}$ are a hydrogen atom.

Examples of the hydrocarbon group having 1 to 10 carbon atoms that may be selected as the R4c include the same hydrocarbon group having 1 to 10 carbon atoms that may be selected as $R^{5a}$ in the general formula (A-2).

The number of carbon atoms of the hydrocarbon group that may be selected as $R^{4c}$ is preferably 1 to 8, more preferably 1 to 6, and still more preferably 1 to 4.

Examples of the alkylene group that may be selected as $R^{5c}$ include the same alkylene group having 2 or more and 4 or less carbon atoms that may be selected as $R^{14a}$ in the general formula (A-1), and a propylene group ($—CH(CH_3)CH_2—$) is preferable.

In the copolymer (A-3-i) or the copolymer (A-3-ii), the content of the oxypropylene unit ($—OCH(CH_3)CH_2—$) is preferably 50 mol % or more and 100 mol % or less, more preferably 65 mol % or more and 100 mol % or less, and still more preferably 80 mol % or more and 100 mol % or less based on the total amount (100 mol %) of oxyalkylene ($OR^{5c}$) which is a structural unit derived from poly(oxy) alkylene glycol or a monoether thereof in the copolymer (A-3-i) or the copolymer (A-3-ii).

Examples of the alkyl group having 1 to 20 carbon atoms that may be selected as $R^{6c}$ include a methyl group, an ethyl group, various propyl groups, various butyl groups, various pentyl groups, various hexyl groups, various heptyl groups, various octyl groups, various nonyl groups, and various decyl groups.

The number of carbon atoms of the alkyl group is preferably 1 to 10, more preferably 1 to 6, and still more preferably 1 to 3.

Examples of the alicyclic group having 3 to 20 ring carbon atoms that may be selected as R& include a cyclopropyl group, a cyclobutyl group, a cyclopentyl group, a cydohexyl group, a cycloheptyl group, a cyclooctyl group, a cyclononyl group, and a cyclodecyl group.

The number of ring carbon atoms of the alicyclic group is preferably 3 to 10, more preferably 3 to 8, and still more preferably 3 to 6.

The alicyclic group may have the aforementioned substituent, and the substituent is preferably an alkyl group.

Examples of the aromatic group having 6 to 24 ring carbon atoms that may be selected as $R^{6c}$ include a phenyl group, a naphthyl group, an anthracenyl group, and a phenanthryl group.

The number of ring carbon atoms of the aromatic group is preferably 6 to 18, and more preferably 6 to 12.

The aromatic group may have the aforementioned substituent, and the substituent is preferably an alkyl group.

Examples of the acyl group having 2 to 20 ring carbon atoms that may be selected as $R^{6c}$ include an acetyl group, a propionyl group, a butyryl group, an isobutyryl group, a valeryl group, an isovaleryl group, a piperoyl group, a benzoyl group, and a toluoyl group.

The number of carbon atoms of the acyl group is preferably 2 to 10, more preferably 2 to 8, and still more preferably 2 to 6.

Examples of the oxygen-containing hydrocarbon group having 2 to 50 carbon atoms that may be selected as $R^{6c}$ include a methoxymethyl group, a methoxyethyl group, a methoxypropyl group, a 1,1-bismethoxypropyl group, a 1,2-bismethoxypropyl group, an ethoxypropyl group, a (2-methoxyethoxy)propyl group, and a (1-methyl-2-methoxy)propyl group.

The number of carbon atoms of the carbon-containing hydrocarbon group is preferably 2 to 20, more preferably 2 to 10, and still more preferably 2 to 6.

Examples of the hydrocarbon group having 1 to 20 carbon atoms that may be selected as $X^C$ and $Y^C$ include an alkyl group having 1 to 20 (preferably 1 to 10, more preferably 1 to 6, and still more preferably 1 to 3) carbon atoms, a substituted or unsubstituted cycloalkyl group having 3 to 20 (preferably 3 to 10, more preferably 3 to 8, and still more preferably 3 to 6) ring carbon atoms, a substituted or unsubstituted phenyl group, a substituted or unsubstituted naphthyl group, and an arylalkyl group having 7 to 20 (preferably 7 to 13) carbon atoms.

(Polyol Ester Compound (POE))

Examples of the POE include esters of diols or polyols with fatty acids. When the base oil (A) contains POE, one kind of POE may be used alone, or two or more kinds of POE may be used in combination.

POE is preferably an ester of a diol or a polyol having 3 to 20 hydroxy groups and a fatty acid having 3 to 20 carbon atoms.

Examples of the diol include ethylene glycol, 1,3-propanediol, propylene glycol, 1,4-butanediol, 1,2-butanediol, 2-methyl-1,3-propanediol, 1,5-pentanediol, neopentyl glycol, 1,6-hexanediol, 2-ethyl-2-methyl-1,3-propanediol, 1,7-heptanediol, 2-methyl-2-propyl-1,3-propanediol, 2,2-diethyl-1,3-propanediol, 1,8-octanediol, 1,9-nonanediol, 1,10-decanediol, 1,11-undecanediol, and 1,12-dodecanediol.

Examples of the polyol include polyhydric alcohols such as trimethylolethane, trimethylolpropane, trimethylolbutane, di-(trimethylolpropane), tri-(trimethylolpropane), pentaerythritol, di-(pentaerythritol), tri-(pentaerythritol), glycerin, polyglycerin (dimer to icosamer of glycerin), 1,3,5-pentanetriol, sorbitol, sorbitan, sorbitol-glycerol condensates, adonitol, arabitol, xylitol, and manitol; sugars such as xylose, arabinose, ribose, rhamnose, glucose, fructose, galactose, mannose, sorbose, cellobiose, maltose, isomaltose, trehalose, sucrose, raffinose, gentianose, and melezitose; partially etherified products thereof; and methyl glucoside (glycoside).

Among these, hindered alcohols such as neopentyl glycol, trimethylolethane, trimethylolpropane, trimethylolbutane, di-(trimethylolpropane), tri-(trimethylolpropane), pentaerythritol, di-(pentaerythritol), and tri-(pentaerythritol) are preferable. The hindered alcohol means an alcohol having a quaternary carbon atom bonded to four carbon atoms.

The number of carbon atoms of the fatty acid is preferably 3 or more, more preferably 4 or more, still more preferably 5 or more, and even more preferably 8 or more from the viewpoint of lubricating performance, and is preferably 20 or less, more preferably 16 or less, still more preferably 12 or less, and even more preferably 10 or less from the viewpoint of the compatibility with a refrigerant.

The number of carbon atoms of the fatty acid includes the carbon atom of the carboxy group (—COOH) of the fatty acid.

The fatty acid may be either a linear fatty acid or a branched fatty acid, but is preferably a linear fatty acid from the viewpoint of lubricating performance, and is preferably a branched fatty acid from the viewpoint of hydrolytic stability. Further, the fatty acid may be either a saturated fatty acid or an unsaturated fatty acid.

Examples of the fatty acid include linear or branched fatty acids such as isobutyric acid, propionic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid, and oleic acid; and so-called neo acids having a quaternary a-carbon atom.

More specifically, isobutyric acid, valeric acid (n-pentanoic acid), caproic acid (n-hexanoic acid), enanthic acid (n-heptanoic acid), caprylic acid (n-octanoic acid), pelargonic acid (n-nonanoic acid), capric acid (n-decanoic acid), oleic acid (cis-9-octadecenoic acid), isopentanoic acid (3-methylbutanoic acid), 2-methylhexanoic acid, 2-ethylpentanoic acid, 2-ethylhexanoic acid, 3,5,5-trimethylhexanoic acid, and the like are preferable.

POE may be a partial ester in which some of the plurality of hydroxy groups of the polyol remain unesterified, or may be a complete ester in which all of the hydroxy groups are esterified. Also, POE may be a mixture of a partial ester and a complete ester, but is preferably a complete ester.

As POE, esters of hindered alcohols such as neopentyl glycol, trimethylolethane, trimethylolpropane, trimethylolbutane, di-(trimethylolpropane), tri-(trimethylolpropane), pentaerythritol, di-(pentaerythritol), and tri-(pentaerythritol) are preferable from the viewpoint of more excellent hydrolytic stability, esters of neopentyl glycol, trimethylolethane, trimethylolpropane, trimethylolbutane, and pentaerythritol are more preferable, and esters of pentaerythritol are still more preferable from the viewpoint of particularly excellent compatibility with a refrigerant and hydrolytic stability.

Specific examples of preferred POE include: diesters of neopentyl glycol with one kind or two or more kinds of fatty acids selected from the group consisting of isobutyric acid, valeric acid, caproic acid, enanthic acid, caprylic acid, pelargonic acid, capric acid, oleic acid, isopentanoic acid, 2-methylhexanoic acid, 2-ethylpentanoic acid, 2-ethylhexanoic acid, and 3,5,5-trimethylhexanoic acid; triesters of trimethylol ethane with one kind or two or more kinds of fatty acids selected from the group consisting of isobutyric acid, valeric acid, caproic acid, enanthic acid, caprylic acid, pelargonic acid, capric acid, oleic acid, isopentanoic acid, 2-methylhexanoic acid, 2-ethylpentanoic acid, 2-ethylhexanoic acid, and 3,5,5-trimethylhexanoic acid; triesters of trimethylolpropane with one kind or two or more kinds of fatty acids selected from the group consisting of isobutyric acid, valeric acid, caproic acid, enanthic acid, caprylic acid, pelargonic acid, capric acid, oleic acid, isopentanoic acid, 2-methylhexanoic acid, 2-ethylpentanoic acid, 2-ethylhexanoic acid, and 3,5,5-trimethylhexanoic acid; triesters of trimethylolbutane with one kind or two or more kinds of fatty acids selected from the group consisting of isobutyric acid, valeric acid, caproic acid, enanthic acid, caprylic acid, pelargonic acid, capric acid, oleic acid, isopentanoic acid, 2-methylhexanoic acid, 2-ethylpentanoic acid, 2-ethylhexanoic acid, and 3,5,5-trimethylhexanoic acid; and tetraesters of pentaerythritol with one kind or two or more kinds of fatty acids selected from the group consisting of isobutyric acid, valeric acid, caproic acid, enanthic acid, caprylic acid, pelargonic acid, capric acid, oleic acid, isopentanoic acid, 2-methylhexanoic acid, 2-ethylpentanoic acid, 2-ethylhexanoic acid, and 3,5,5-trimethylhexanoic acid.

The ester of two or more kinds of fatty acids may be a mixture of two or more kinds of esters of one kind of fatty acid and a polyol. Among POE's, an ester of a mixture of two or more kinds of fatty acids and a polyol is preferable from the viewpoint of improvement in low-temperature characteristics and the compatibility with a refrigerant.

(Preferred Aspect of Base Oil (A))

In the refrigerator oil composition of the present embodiment, from the viewpoint of long-term stability required as a refrigerator oil composition, the main component of the base oil (A) is preferably the above-described base oil (A1), and more preferably the above-described base oil (A2). In addition, the term "main component" as used herein means a component having the largest content.

The content of the base oil (A1) or the base oil (A2) in the base oil (A) is preferably 50% by mass to 100% by mass, more preferably 60% by mass to 100% by mass, still more preferably 70% by mass to 100% by mass, even more preferably 80% by mass to 100% by mass, yet still more preferably 90% by mass to 100% by mass, and yet even more preferably 100% by mass based on the total amount (100% by mass) of the base oil (A).

Here, the base oil (A1) is preferably PAG, PVE, ECP, or POE (i.e. consists only of PAG, PVE, ECP, or POE).

Therefore, the content of PAG, PVE, ECP, or POE in the base oil (A) is preferably 50% by mass to 100% by mass, more preferably 60% by mass to 100% by mass, still more preferably 70% by mass to 100% by mass, even more preferably 80% by mass to 100% by mass, yet still more preferably 90% by mass to 100% by mass, and yet even more preferably 100% by mass based on the total amount (100% by mass) of the base oil (A).

Further, from the viewpoint of long-term stability required as a refrigerator oil composition, it is preferable that the base oil (A2) is PAG or PVE (that is, consists only of PAG or PVE).

Therefore, the content of PAG or PVE in the base oil (A) is preferably 50% by mass to 100% by mass, more preferably 60% by mass to 100% by mass, still more preferably 70% by mass to 100% by mass, even more preferably 80% by mass to 100% by mass, yet still more preferably 90% by mass to 100% by mass, and yet even more preferably 100% by mass based on the total amount (100% by mass) of the base oil (A).

(Other Base Oil)

The base oil (A) may further contain other base oils as long as the effects of the present invention are not impaired.

Examples of other base oils include one or more kinds selected from the group consisting of mineral oils and synthetic oils that do not fall under the aforementioned PVE, PAG, ECP, and POE.

Examples of the mineral oil include a refined oil obtained by subjecting a lubricating oil fraction obtained through distillation under reduced pressure on an atmospheric residual oil obtained by distilling a paraffinic crude oil, an intermediate-based crude oil, or a naphthene-based crude oil at atmospheric pressure or distilling a crude oil at atmospheric pressure, to at least one of treatments such as solvent deasphalting, solvent extraction, hydrocracking, solvent dewaxing, catalytic dewaxing, and hydrorefining; and an oil produced by isomerizing mineral oil-based wax.

When the mineral oil is contained in the base oil (A), one type of the mineral oil may be used alone, or two or more types of the mineral oil may be used in combination.

Examples of the synthetic oils that do not fall under the aforementioned PVE, PAG, ECP, and POE include polyesters, polycarbonates, hydrogenated α-olefin oligomers, alicyclic hydrocarbon compounds, alkylated aromatic hydrocarbon compounds, and oils produced by isomerization of GTL WAX (gas-to-liquid wax) produced by the Fischer-Tropsch process or the like.

When the synthetic oil that does not fall under the aforementioned PVE, PAG, ECP, and POE is contained in the base oil (A), one type of the synthetic oil may be used alone, or two or more types of the synthetic oil may be used in combination.

In the refrigerator oil composition of the present embodiment, the content of the mineral oil is preferably small from the viewpoint of solubility of the epoxy compound (B). Specifically, the content of the mineral oil is preferably 10% by mass or less, more preferably 1% by mass or less, and still more preferably 0.1% by mass or less based on the total amount of the base oil (A), and even more preferably no mineral oil is contained.

(100° C. Kinematic Viscosity of Base Oil (A))

The 100° C. kinematic viscosity of the base oil (A) is preferably 3 $mm^2/s$ or more, more preferably 4 $mm^2/s$ or more, and still more preferably 5 $mm^2/s$ or more, from the viewpoint of improving the lubricating performance (load bearing performance) and the sealing property. On the other hand, from the viewpoint of improving the compatibility with a refrigerant, it is preferably 50 $mm^2/s$ or less, more preferably 40 $mm^2/s$ or less, and still more preferably 30 $mm^2/s$ or less.

The upper limit values and the lower limit values of these numerical ranges can be arbitrarily combined. Specifically, it is preferably 3 $mm^2/s$ to 50 $mm^2/s$, more preferably 4 $mm^2/s$ to 40 $mm^2/s$, and still more preferably 5 $mm^2/s$ to 30 $mm^2/s$.

In the description herein, the value of the 100° C. kinematic viscosity of the base oil (A) is a value measured in accordance with JIS K 2283:2000.

(Hydroxyl Value of Base Oil (A))

The hydroxyl value of the base oil (A) is preferably 30 mgKOH/g or less, more preferably 25 mgKOH/g or less, and still more preferably 20 mgKOH/g or less from the viewpoint of improving the thermal stability of the refrigerator oil composition. On the other hand, it is usually 0.5 mgKOH/g or more.

In the description herein, the value of the hydroxyl value of the base oil (A) is a value measured by a neutralization titration method in accordance with JIS K 0070:1992.

(Number Average Molecular Weight (Mn) of Base Oil (A))

The number average molecular weight (Mn) of the base oil (A) is preferably 300 or more, more preferably 400 or more, and still more preferably 500 or more, from the viewpoint of improving the lubricating performance (load bearing performance) and the sealing property. On the other hand, from the viewpoint of improving the compatibility with a refrigerant, it is preferably 10,000 or less, more preferably 7,000 or less, and still more preferably 5,000 or less.

The upper limit values and the lower limit values of these numerical ranges can be arbitrarily combined. Specifically, it is preferably 300 to 10,000, more preferably 400 to 7,000, and still more preferably 500 to 5,000.

In the description herein, the value of the number average molecular weight (Mn) of the base oil (A) is a value measured by the method described in Examples described later.

<Epoxy Compound (B)>

The refrigerator oil composition of the present embodiment contains an epoxy compound (B) satisfying the following requirements (B1) and (B2):

(B1) at least one divalent group represented by the following formula (1) is present in the molecule;

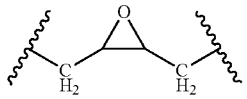

(1)

(B2) at least one ester group is present in the molecule.

The group represented by the above formula (1) contained in the epoxy compound (B) is less likely to decompose an unsaturated fluorinated hydrocarbon compound (HFO) than an epoxy compound having a structure having an epoxy group at a molecular terminal, less likely to generate a fluorine component (for example, hydrofluoric acid) generated by the decomposition of the unsaturated fluorinated hydrocarbon compound (HFO) under a high-temperature environment, and the small amount of the generated fluorine component reacts with the epoxy group in the epoxy compound (B) and is captured in the epoxy compound (B). It is presumed that the elution of the fluorine component into the refrigerator oil composition is suppressed by these functions, and since the eluted fluorine component can be captured, an increase in the acid value of the refrigerator oil composition can be suppressed.

The epoxy compound (B) preferably has a molecular weight of 300 or more because the reactivity of the epoxy group can be moderately suppressed, the decomposition of the unsaturated fluorinated hydrocarbon compound can be suppressed, and the solubility in the base oil is improved, and more preferably 350 or more.

On the other hand, the molecular weight of the epoxy compound (B) is preferably 2000 or less, more preferably 1500 or less, and still more preferably 1000 or less, from the viewpoint of solubility in a refrigerator oil and generation of sludge after stability evaluation.

In the refrigerator oil composition of the present embodiment, from the viewpoint of more easily exhibiting the effect of suppressing an increase in the acid value of the refrigerator oil composition, the content of the epoxy compound (B) is preferably 0.10% by mass or more, more preferably 0.20% by mass or more, still more preferably 0.50% by mass or more, and even more preferably 1.00% by mass or more based on the total amount (100% by mass) of the refrigerator oil composition. The upper limit of the content of the epoxy compound (B) is not particularly limited, but is preferably 10.00% by mass or less, more preferably 7.00% by mass or less, and still more preferably 5.00% by mass or less, from the viewpoint of obtaining an effect commensurate with the addition amount.

The upper limit values and the lower limit values of these numerical ranges can be arbitrarily combined. Specifically, the content is preferably 0.10% by mass to 10.00% by mass, more preferably 0.20% by mass to 7.00% by mass, still more preferably 0.50% by mass to 5.00% by mass, and even more preferably 1.00% by mass to 5.00% by mass.

In the present embodiment, as the epoxy compound (B), one or more kinds selected from the group consisting of those satisfying the above two requirements can be used without particular limitation.

Specific examples of the epoxy compound (B) include an epoxidized fatty acid ester, an epoxidized alicyclic carboxylic acid ester, and an epoxidized vegetable oil, which satisfy the above requirements (B1) and (B2).

(Epoxidized Fatty Acid Ester)

Examples of the epoxidized fatty acid ester include those obtained by epoxidation of an ester of a fatty acid having 8 to 30 carbon atoms (preferably 12 to 20 carbon atoms) and an alcohol having 1 to 8 carbon atoms, a phenol, or an alkylphenol having 7 to 14 carbon atoms.

As the epoxidized fatty acid ester, those represented by the following general formula (1-1) are preferably used from the viewpoint of effectively suppressing an increase in the acid value of the refrigerator oil composition.

(1-1)

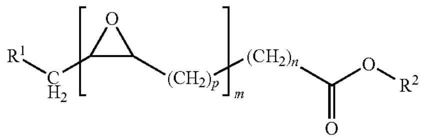

(In the formula (1-1), R1 is a hydrocarbon group having 4 to 20 carbon atoms, R2 is a hydrocarbon group having 1 to 10 carbon atoms, p is an integer of 1 to 3, n is an integer of 0 to 12, m is an integer of 1 to 3, and when m is 2 or more, a plurality of structures in brackets [ ] may be the same as or different from each other.)

Examples of the hydrocarbon group include alkyl groups such as a methyl group, an ethyl group, a n-propyl group, an isopropyl group, various butyl groups, various pentyl groups, various hexyl groups, various heptyl groups, various octyl groups, various nonyl groups, and various decyl groups; cycloalkyl groups such as a cyclopentyl group, a cyclohexyl group, various methylcyclohexyl groups, various ethylcyclohexyl groups, various propylcyclohexyl groups, and various dimethylcyclohexyl groups; aryl groups such as a phenyl group, various methylphenyl groups, various ethylphenyl groups, various dimethylphenyl groups, various propylphenyl groups, various trimethylphenyl groups, various butylphenyl groups, and various naphthyl groups; and arylalkyl groups such as a benzyl group, various phenylethyl groups, various methylbenzyl groups, various phenylpropyl groups, and various phenylbutyl groups, each of which has the corresponding number of carbon atoms.

In the epoxidized fatty acid esters represented by the formula (1-1), those in which R1 is an alkyl group having 5 to 12 carbon atoms, R2 is an alkyl group having 1 to 6 carbon atoms, p is 1, n is an integer of 1 to 10, and m is 1 or 2 are preferable.

Specific examples of the epoxidized fatty acid ester include those obtained by epoxidation of butyl ester, hexyl ester, 2-ethylhexyl ester, benzyl ester, cyclohexyl ester, methoxyethyl ester, octyl ester, phenyl ester, or butyl phenyl ester of linoleic acid, oleic acid, palmitic acid, linolenic acid, or stearic acid.

Examples of commercially available products of the epoxidized vegetable oil include SANSO CIZER E-6000 manufactured by New Japan Chemical Co., Ltd. and Chemicizer T-5000 manufactured by Sanwa Gouseikagaku Co., Ltd.

(Epoxidized Alicyclic Carboxylic Acid Ester)

Examples of the epoxidized alicyclic carboxylic acid ester include those obtained by epoxidation of an ester of an alicyclic carboxylic acid having 5 to 12 ring carbon atoms and an alcohol having 1 to 8 carbon atoms, a phenol, or an alkyl phenol having 7 to 14 carbon atoms, and the alicyclic carboxylic acid may be a monocarboxylic acid or a dicarboxylic acid.

As the epoxidized alicyclic carboxylic acid ester, those represented by the following general formula (1-2) are preferably used from the viewpoint of effectively suppressing an increase in the acid value of the refrigerator oil composition.

(1-2)

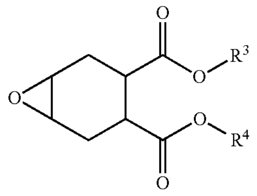

(In the formula (1-2), R3 and R4 are each independently a hydrocarbon group having 4 to 20 carbon atoms.)

Specific examples of the hydrocarbon group include those having the corresponding number of carbon atoms from those listed as hydrocarbon groups in the formula (1-1).

In the epoxidized alicyclic carboxylic acid esters represented by the formula (1-2), those in which R3 and R4 are each independently an alkyl group having 6 to 12 carbon atoms are preferable.

Specific examples of the epoxidized alicyclic carboxylic acid ester include epoxidized alicyclic dicarboxylic acid esters, and more specific examples include 4,5-epoxycyclohexane-1,2-dicarboxylic acid di-2-ethylhexyl.

Examples of commercially available products of the epoxidized alicyclic carboxylic acid ester include SANSO CIZER E-PS manufactured by New Japan Chemical Co., Ltd.

(Epoxidized Vegetable Oil)

Examples of the epoxidized vegetable oil include those obtained by epoxidation of vegetable oils such as soybean oil, linseed oil, rice bran oil, and cottonseed oil.

As the epoxidized vegetable oils, those having a group represented by the following general formula (1-3) are preferably used from the viewpoint of effectively suppressing an increase in the acid value of the refrigerator oil composition; more specifically, glycerin esters having one or more groups represented by the following general formula (1-3) are preferable, triglycerides having one or more groups represented by the following general formula (1-3) are more preferable, and triglycerides having two or more groups represented by the following general formula (1-3) are still more preferable.

(1-3)

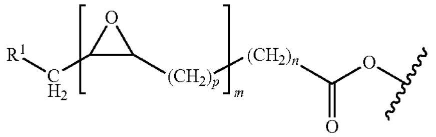

(In the formula (1-3), R1 is a hydrocarbon group having 4 to 20 carbon atoms, p is an integer of 1 to 3, n is an integer of 0 to 12, m is an integer of 1 to 3, and when m is 2 or more, a plurality of structures in brackets [ ] may be the same as or different from each other.)

The details of $R^1$ are the same as those in the formula (1-1).

In the groups represented by the formula (1-3), those in which $R^1$ is an alkyl group having 5 to 12 carbon atoms, p is 1, n is an integer of 1 to 10, and m is 1 or 2 are preferable.

Examples of commercially available products of the epoxidized vegetable oil include SANSO CIZER E-2000H manufactured by New Japan Chemical Co., Ltd., Chemicizer SE-80, Chemicizer SE-100, Chemicizer T-3000N, Chemicizer LE-3000, and Chemicizer T-2000 manufactured by Sanwa Gouseikagaku Co., Ltd., Newcizer 510R manufactured by NOF Corporation, and Adekacizer O-180A manufactured by Adeka Corporation.

<Glycidyl Ether Compound (C)>

The refrigerator oil composition of the present embodiment may further contain a glycidyl ether compound (C).

Examples of the glycidyl ether compound (C) include a glycidyl ether derived from an aliphatic mono or polyhydric alcohol having a number of carbon atoms of usually 3 to 30, preferably 4 to 24, and more preferably 6 to 16, or an aromatic compound containing one or more hydroxy groups. The aliphatic mono or polyhydric alcohol may be linear, branched, or cyclic, and may be saturated or unsaturated, but is preferably a saturated aliphatic monoalcohol.

In the case of an aliphatic polyhydric alcohol or an aromatic compound containing two or more hydroxy groups, all of the hydroxy groups are preferably glycidyl-etherified from the viewpoint of stability of the refrigerator oil composition.

Examples of the glycidyl ether compound include phenyl glycidyl ether, alkyl glycidyl ether, and alkylene glycol glycidyl ether. Among these, a glycidyl ether derived from a linear, branched, or cyclic saturated aliphatic monoalcohol having 6 to 16 carbon atoms (i.e., an alkyl glycidyl ether having an alkyl group having 6 to 16 carbon atoms) is more preferable. Examples of such glycidyl ether include 2-ethylhexyl glycidyl ether, isononyl glycidyl ether, decyl glycidyl ether, lauryl glycidyl ether, and myristyl glycidyl ether, and 2-ethylhexyl glycidyl ether is most preferable. By using an alkyl glycidyl ether such as 2-ethylhexyl glycidyl ether, an increase in the acid value of the refrigerator oil composition can be appropriately prevented, and the oxidation stability at high temperatures can be more easily improved.

The content of the glycidyl ether compound (C) is preferably 0.10 to 10.00% by mass based on the total amount of the refrigerator oil composition. By setting the content of the glycidyl ether compound (C) to 0.10% by mass or more, the acid in the refrigerator oil composition can be appropriately trapped, an increase in the acid value of the refrigerator oil composition can be effectively prevented, and high-temperature stability can be easily improved. Further, by setting the content of the glycidyl ether compound (C) to 10.00% by mass or less, an effect commensurate with the content can be achieved.

The content of the glycidyl ether compound (C) is more preferably 0.4% by mass or more, and still more preferably 0.5% by mass or more. On the other hand, it is more preferably 5% by mass or less, still more preferably 4% by mass or less, and even more preferably 3% by mass or less. The upper limit values and the lower limit values of these numerical ranges can be arbitrarily combined. Specifically, it is more preferably 0.4% by mass to 5% by mass, still more preferably 0.5% by mass to 4% by mass, and even more preferably 0.5% by mass to 3% by mass. The glycidyl ether compound (C) may be used alone or in combination of two or more kinds thereof.

<Content Ratio of Epoxy Compound (B) to Glycidyl Ether Compound (C)>

In the refrigerator oil composition of the present embodiment, the content ratio [(B)/(C)] of the epoxy compound (B) to the glycidyl ether compound (C) is preferably 0.050 or more, more preferably 0.10 or more, and still more preferably 0.20 or more, and is preferably 5.0 or less, more preferably 3.5 or less, and still more preferably 2.5 or less in terms of mass ratio, from the viewpoint of more easily exhibiting the effects of the present invention.

The upper limit values and the lower limit values of these numerical ranges can be arbitrarily combined. Specifically, it is preferably 0.050 to 5.0, more preferably 0.10 to 3.5, and still more preferably 0.20 to 2.5.

<Other Additives>

The refrigerator oil composition of the present embodiment may further contain other additives in addition to the components (A), (B), and (C) as long as the effects of the present invention are not impaired.

Examples of the other additives include one or more selected from the group consisting of an antioxidant, a stabilizer, an extreme pressure agent, and an anti-foaming agent.

The total content of these additives is preferably 0% by mass to 10% by mass, more preferably 0.01% by mass to 5% by mass, and still more preferably 0.1% by mass to 3% by mass, based on the total amount (100% by mass) of the refrigerator oil composition.

(Antioxidant)

The antioxidant is preferably one or more selected from the group consisting of a phenol-based antioxidant and an amine-based antioxidant.

Examples of the phenol-based antioxidant include 2,6-di-tert-butyl-p-cresol (DBPC), 2,6-di-tert-butyl-4-ethylphenol, and 2,2'-methylenebis(4-methyl-6-tert-butylphenol).

Examples of the amine-based antioxidant include phenyl-α-naphthylamine and N,N'-diphenyl-p-phenylenediamine.

Among these, a phenol-based antioxidant is preferable, and among the phenol-based antioxidants, 2,6-di-tert-butyl-p-cresol (DBPC) is preferable.

The content of the antioxidant is preferably 0.01% by mass or more, more preferably 0.05% by mass or more, and still more preferably 0.1% by mass or more based on the total amount (100% by mass) of the refrigerator oil composition, from the viewpoint of stabilization and anti-oxidation performance. On the other hand, it is preferably 5% by mass or less, more preferably 3% by mass or less, and still more preferably 1% by mass or less.

The upper limit values and the lower limit values of these numerical ranges can be arbitrarily combined. Specifically, the content is preferably 0.01% by mass to 5% by mass, more preferably 0.05% by mass to 3% by mass, and still more preferably 0.1% by mass to 1% by mass.

(Stabilizer)

Examples of the stabilizer include aliphatic unsaturated compounds and terpenes having a double bond.

As the aliphatic unsaturated compound, unsaturated hydrocarbons are preferable, and specific examples thereof include olefins, and polyenes such as dienes and trienes. As the olefin, from the viewpoint of reactivity with oxygen, α-olefins such as 1-tetradecene, 1-hexadecene, and 1-octadecene are preferable.

As the aliphatic unsaturated compound other than the above, an unsaturated aliphatic alcohol having a conjugated double bond such as vitamin A ((2E,4E,6E,8E)-3,7-dimethyl-9-(2,6,6-trimethylcyclohexe-1-yl)nona-2,4,6,8-tetraen-1-ol) represented by molecular formula $C_{20}H_{30}O$ is preferable from the viewpoint of reactivity with oxygen.

As the terpenes having a double bond, terpene-based hydrocarbons having a double bond are preferable, and a-pinene, B-pinene, a-farnesene ($C_{15}H_{24}$: 3,7,11-trimethyldodeca-1,3,6,10-tetraene), and B-farnesene ($C_{15}H_{24}$: 7,11-dimethyl-3-methylidenedodeca-1,6,10-triene) are more preferable from the viewpoint of reactivity with oxygen.

The stabilizer may be used alone or in combination of two or more kinds thereof.

(Extreme Pressure Agent)

As the extreme pressure agent, a phosphorus-based extreme pressure agent, a metal salt of a carboxylic acid, and a sulfur-based extreme pressure agent are preferable.

Examples of the phosphorus-based extreme pressure agent include phosphoric acid esters, acidic phosphoric acid esters, phosphorous acid esters, acidic phosphorous acid esters, and amine salts thereof.

Among these, from the viewpoint of improving the extreme pressure properties and the friction characteristics, one or more selected from tricresyl phosphate (TCP), trithiophenyl phosphate, tri(nonylphenyl) phosphite, dioleyl hydrogen phosphite, and 2-ethylhexyl diphenyl phosphite are preferable, and tricresyl phosphate (TCP) is more preferable.

Examples of the metal salt of a carboxylic acid include a metal salt of a carboxylic acid having 3 to 60 carbon atoms (preferably 3 to 30 carbon atoms).

Among these, one or more selected from a fatty acid having 12 to 30 carbon atoms and a metal salt of a dicarboxylic acid having 3 to 30 carbon atoms are preferable.

In addition, as the metal constituting the metal salt, an alkali metal and an alkaline earth metal are preferable, and an alkali metal is more preferable.

Examples of the sulfur-based extreme pressure agent include sulfurized oils and fats, sulfurized fatty acids, sulfurized esters, sulfurized olefins, dihydrocarbyl polysulfides, thiocarbamates, thioterpenes, and dialkyl thiodipropionates.

From the viewpoint of lubricity and stability, the content of the extreme pressure agent is preferably 0.001 to 5% by mass, and more preferably 0.005 to 3% by mass based on the total amount (100% by mass) of the refrigerator oil composition.

(Anti-foaming Agent)

Examples of the anti-foaming agent include silicone-based anti-foaming agents such as silicone oil and fluorinated silicone oil.

[Method for Producing Refrigerator Oil Composition]

The method for producing the refrigerator oil composition is not particularly limited.

For example, the method for producing a refrigerator oil composition of the present embodiment is a method for producing a refrigerator oil composition used for a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule]

the method including a step of mixing a base oil (A) and an epoxy compound (B), wherein the epoxy compound (B) satisfies the following requirements (B1) and (B2):

(B1) at least one oxirane-2,3-diyl group is present in the molecule;

(B2) at least one ester group is present in the molecule.

The method for mixing the above components is not particularly limited, and examples thereof include a method including a step of blending the epoxy compound (B) into the base oil (A). The glycidyl ether compound (C) and the other additives may be added to the base oil (A) at the same time as the epoxy compound (B), or may be added separately. Each component may be blended after it is in the form of a solution (dispersion) by adding a diluent oil or the like. After each component is blended, it is preferable to uniformly disperse the components by stirring according to a known method.

[Physical Properties of Refrigerator Oil Composition]

In the present embodiment, the physical property values of refrigerator oil composition after performing an autoclave test described in Examples described later are as follows.

<Acid Value>

The acid value of the refrigerator oil composition after an autoclave test described in Examples described later is preferably 0.15 mgKOH/g or less, and more preferably 0.10 mgKOH/g or less.

<Fluorine Amount>

The fluorine amount in the refrigerator oil composition after an autoclave test described in Examples described later is preferably 15 ppm by mass or less, more preferably 10 ppm by mass or less, and still more preferably 7 ppm by mass or less based on the total amount of the refrigerator oil composition.

[Refrigerator Oil Mixture Composition]

The refrigerator oil composition is mixed with a refrigerant and used as a refrigerator oil mixture composition.

That is, the refrigerator oil mixture composition contains the refrigerator oil composition and a refrigerant.

The refrigerant will be described below.

<Refrigerant>

The refrigerant used in the present embodiment is a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule].

The general formula (1) represents the types and numbers of elements in the molecule, and specifically represents an unsaturated fluorinated hydrocarbon compound having 2 to 6 carbon atoms C. The unsaturated fluorinated hydrocarbon compound having 2 to 6 carbon atoms has physical and chemical properties such as a boiling point, a freezing point, and latent heat of vaporization required as a refrigerant.

In the general formula (1), examples of the bonding form of x carbon atoms represented by $C_x$ include a carbon-carbon single bond and an unsaturated bond such as a carbon-carbon double bond. The carbon-carbon unsaturated bond is preferably a carbon-carbon double bond from the viewpoint of stability, and the unsaturated fluorinated hydrocarbon compound preferably has one or more unsaturated bonds such as a carbon-carbon double bond in the molecule, and the number thereof is preferably one. That is, at least one of the bonding forms of the x carbon atoms represented by $C_x$ is more preferably a carbon-carbon double bond.

Preferable examples of the unsaturated fluorinated hydrocarbon compound include a fluoride of a linear or branched chain olefin having 2 to 6 carbon atoms and a fluoride of a cyclic olefin having 4 to 6 carbon atoms.

Specific examples thereof include a fluoride of ethylene into which 1 to 3 fluorine atoms have been introduced, a fluoride of propene into which 1 to 5 fluorine atoms have been introduced, a fluoride of butene into which 1 to 7 fluorine atoms have been introduced, a fluoride of pentene into which 1 to 9 fluorine atoms have been introduced, a fluoride of hexene into which 1 to 11 fluorine atoms have been introduced, a fluoride of cyclobutene into which 1 to 5 fluorine atoms have been introduced, a fluoride of cyclopentene into which 1 to 7 fluorine atoms have been introduced, and a fluoride of cyclohexene into which 1 to 9 fluorine atoms have been introduced.

Among these, a fluoride of propene is preferable, and a fluoride of propene into which 3 to 5 fluorine atoms are introduced is more preferable. Specifically, one or more selected from 1,3,3,3-tetrafluoropropene (R1234ze), 2,3,3,3-tetrafluoropropene (R1234yf), and 1,2,3,3-tetrafluoropropene (R1234ye) are preferable, and 2,3,3,3-tetrafluoropropene (R1234yf) is more preferable.

The unsaturated fluorinated hydrocarbon compounds may be used alone or in combination of two or more kinds thereof. Therefore, only one selected from 1,3,3,3-tetrafluoropropene (R1234ze), 2,3,3,3-tetrafluoropropene (R1234yf), and 1,2,3,3-tetrafluoropropene (R1234ye) may be used alone.

(Other Refrigerant)

In the present embodiment, the refrigerant may be a mixed refrigerant containing other compounds as necessary in addition to the unsaturated fluorinated hydrocarbon compound represented by the general formula (1), and may contain, for example, a saturated fluorinated hydrocarbon compound.

The saturated fluorinated hydrocarbon compound is preferably a fluoride of an alkane having 1 to 4 carbon atoms, more preferably a fluoride of an alkane having 1 to 3 carbon atoms, and still more preferably a fluoride of an alkane having 1 or 2 carbon atoms (methane or ethane). Examples of the fluoride of methane or ethane include trifluoromethane (R23), difluoromethane (R32), 1,1-difluoroethane (R152a), 1,1,1-trifluoroethane (R143a), 1,1,2-trifluoroethane (R143), 1,1,1,2-tetrafluoroethane (R134a), 1,1,2,2-tetrafluoroethane (R134), and 1, 1,1,2,2-pentafluoroethane (R125). Among these, difluoromethane and 1,1,1,2,2-pentafluoroethane are preferable.

These saturated fluorinated hydrocarbon compounds may be used alone or in combination of two or more kinds thereof.

Further, the refrigerant may include a natural refrigerant. Examples of the natural refrigerant include hydrocarbon refrigerants (HC), carbon dioxide ($CO_2$, carbon dioxide), and ammonia. These natural refrigerants may be used alone or in combination of two or more kinds thereof.

The hydrocarbon refrigerant is preferably a hydrocarbon having 1 or more and 8 or less carbon atoms, more preferably a hydrocarbon having 1 or more and 5 or less carbon atoms, and still more preferably a hydrocarbon having 3 or more and 5 or less carbon atoms. When the number of carbon atoms is 8 or less, the boiling point of the refrigerant does not become too high, which is preferable as a refrigerant. Examples of the hydrocarbon-based refrigerant include one or more selected from the group consisting of methane, ethane, ethylene, propane (R290), cyclopropane, propylene, n-butane, isobutane (R600a), 2-methylbutane, n-pentane, isopentane, cyclopentaneisobutane, and n-hexane, and these may be used alone or in combination of two or more thereof.

(Content of Unsaturated Fluorinated Hydrocarbon Compound in Refrigerant)

In the present embodiment, the refrigerant contains the unsaturated fluorinated hydrocarbon compound represented by the general formula (1).

The content of the unsaturated fluorinated hydrocarbon compound represented by the general formula (1) is preferably 50% by mass to 100% by mass, more preferably 60% by mass to 100% by mass, still more preferably 70% by mass to 100% by mass, even more preferably 80% by mass to 100% by mass, yet still more preferably 90% by mass to 100% by mass, and yet even more preferably 100% by mass based on the total amount of the refrigerant.

The refrigerator oil composition of the present embodiment is excellent in the effect of suppressing an increase in the acid value even when the refrigerant has a high content of the unsaturated fluorinated hydrocarbon compound.

(Amount of Refrigerant and Refrigerator Oil Composition Used)

In the refrigerator oil mixture composition of the present embodiment, the amount of the refrigerant and the refrigerator oil composition used is preferably 1/99 to 90/10, and more preferably 5/95 to 70/30 in terms of the mass ratio of the refrigerator oil composition the refrigerant [(refrigerator oil to composition)/(refrigerant)]. When the mass ratio of the refrigerator oil composition to the refrigerant is within the above range, lubricity and suitable refrigerating capacity in the refrigerator can be obtained.

[Use of Refrigerator Oil Composition and Refrigerator Oil Mixture Composition]

The refrigerator oil composition and the refrigerator oil mixture composition are preferably used in, for example, air conditioners, cold storages, vending machines, showcases, refrigeration systems, hot water supply systems, or heating systems. Examples of the air conditioner include a car air conditioner such as an open type car air conditioner and an electric car air conditioner; and a gas heat pump (GHP) air conditioner.

[One Aspect of the Invention Provided]

According to one aspect of the present invention, the following [1] to are provided.

[1] A refrigerator oil composition used for a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule], the refrigerator oil composition containing a base oil (A) selected from the group consisting of a polyalkylene glycol compound, a polyvinyl ether compound, a copolymer of poly(oxy)alkylene glycol or a monoether thereof and polyvinyl ether, and a polyol ester compound; and an epoxy compound (B), wherein the epoxy compound (B) satisfies the following requirements (B1) and (B2):

(B1) at least one divalent group represented by the following formula (1) is present in the molecule;

(1)

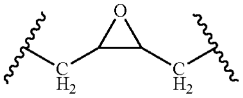

(B2) at least one ester group is present in the molecule.

[2] The refrigerator oil composition as set forth in [1], wherein the epoxy compound (B) has a molecular weight of 300 or more.

[3] The refrigerator oil composition as set forth in [1] or [2], wherein a content of the epoxy compound (B) is 0.10% by mass or more based on the total amount of the refrigerator oil composition.

[4] The refrigerator oil composition as set forth in any of [1] to [3], wherein the epoxy compound (B) is one or more selected from the group consisting of an epoxidized fatty acid ester, an epoxidized alicyclic carboxylic acid ester, and an epoxidized vegetable oil.

[5] The refrigerator oil composition as set forth in [4], wherein the epoxidized fatty acid ester is represented by the following general formula (1-1):

(1-1)

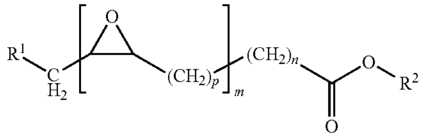

wherein R1 is a hydrocarbon group having 4 to 20 carbon atoms, R2 is a hydrocarbon group having 1 to 10 carbon atoms, p is an integer of 1 to 3, n is an integer of 0 to 12, m is an integer of 1 to 3, and when m is 2 or more, a plurality of structures in brackets [ ] may be the same as or different from each other.

[6] The refrigerator oil composition as set forth in [4], wherein the epoxidized alicyclic carboxylic acid ester is represented by the following general formula (1-2):

(1-2)

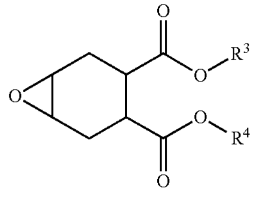

wherein $R^3$ and R4 are each independently a hydrocarbon group having 4 to 20 carbon atoms.

[7] The refrigerator oil composition as set forth in [4], wherein the epoxidized vegetable oil is one or more selected from the group consisting of an epoxidized soybean oil, an epoxidized linseed oil, an epoxidized rice bran oil, and an epoxidized cottonseed oil.

[8] The refrigerator oil composition as set forth in any of [1] to [7], further containing a glycidyl ether compound (C).

[9] The refrigerator oil composition as set forth in [8], wherein a content ratio [(B)/(C)] of the epoxy compound (B) to the glycidyl ether compound (C) is 0.050 or more and 5.0 or less in terms of mass ratio.

[10] The refrigerator oil composition as set forth in any of [1] to [9], further containing one or more additives selected from the group consisting of an antioxidant, a stabilizer, an extreme pressure agent, and an anti-foaming agent.

[11] The refrigerator oil composition as set forth in any of [1] to [10], wherein the unsaturated fluorinated hydrocarbon compound contains one or more selected from the group consisting of R1234ze, R1234yf, and R1234ye.

[12] The refrigerator oil composition as set forth in any of [1] to [11], wherein the refrigerant consists only of the unsaturated fluorinated hydrocarbon compound.

[13] A refrigerator oil mixture composition containing: a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule]; and the refrigerator oil composition as set forth in any of [1] to [12].

[14] A method for producing a refrigerator oil composition used for a refrigerant containing one or more unsaturated fluorinated hydrocarbon compounds selected from compounds represented by the following general formula (1):

$$C_xF_yH_z \quad (1)$$

[wherein x is an integer of 2 to 6, y is an integer of 1 to 11, and z is an integer of 1 to 11, and one or more carbon-carbon unsaturated bonds are present in the molecule], the method including a step of mixing a base oil (A) selected from the group consisting of a polyalkylene glycol compound, a polyvinyl ether compound, a copolymer of poly(oxy)alkylene glycol or a monoether thereof and polyvinyl ether, and a polyol ester compound; and an epoxy compound (B), wherein the epoxy compound (B) satisfies the following requirements (B1) and (B2):

(B1) at least one divalent group represented by the following formula (1) is present in the molecule;

(1)

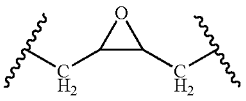

(B2) at least one ester group is present in the molecule.

EXAMPLES

The present invention will be specifically described with reference to the following examples. However, the present invention is not limited to the following examples.

[Measurement Method of Various Physical Properties]

The raw materials used in Examples and Comparative Examples and the properties of the refrigerator oil compositions of Examples and Comparative Examples were measured in the following manner.

(1) 100° C. Kinematic viscosity

The 100° C. kinematic viscosity of the base oil (A) was measured in accordance with JIS K 2283:2000.

(2) Hydroxyl value

The hydroxyl value of the base oil (A) was measured by a neutralization titration method in accordance with JIS K 0070: 1992.

(3) Number average molecular weight (Mn)

The number average molecular weight (Mn) of the base oil (A) was measured by using a gel permeation chromatography (GPC) apparatus.

In the GPC, two columns of "TSKgel SuperMultiporeHZ-M" manufactured by Tosoh Corporation were connected in order were used as columns, tetrahydrofuran was used as an eluent, and a refractive index detector (RI detector) was used as a detector, and the number average molecular weight (Mn) was determined using polystyrene as a standard sample.

[Details of Each Component Used for Preparation of Refrigerator Oil Composition]

Details of each component used in the preparation of the refrigerator oil composition are provided below.

<Base Oil (A)>

"PVE1": polyvinyl ether (a copolymer of polyethyl vinyl ether (PEVE) and polyisobutyl vinyl ether (PIBVE), copolymerization ratio (PEVE/PIBVE)=9/1 (molar ratio)), 100° C. kinematic viscosity=8.4 $mm^2/s$, hydroxyl value=1 mgKOH/g, number average molecular weight=940.

"PVE2": polyethyl vinyl ether, 100° C. kinematic viscosity=8.6 $mm^2/s$, hydroxyl value=1 mgKOH/g, number average molecular weight=1100.

"PAG": polyoxypropylene glycol, 100° C. kinematic viscosity=10.3 $mm^2/s$, hydroxyl value=6 mgKOH/g, number average molecular weight=1020.

"ECP": a copolymer of polypropylene glycol (PPG) and polyethyl vinyl ether (PEV) (PPG/PEV=5/5 (molar ratio)), 100° C. kinematic viscosity=10.5 $mm^2/s$, hydroxyl value=1 mgKOH/g, number average molecular weight=870.

"POE": an ester of pentaerythritol with a mixture of octanoic acid (C8 acid) and nonanoic acid (C9 acid) (C8 acid/C9 acid=1/1.1 (molar ratio)), 100° C. kinematic viscosity=8.5 $mm^2/s$, hydroxyl value=1 mgKOH/g, number average molecular weight=670.

<Epoxy Compound (B)>

"Epoxy Compound 1": an epoxidized soy bean oil represented by the following formula, molecular weight: 933, SANSO CIZER E-2000H (manufactured by New Japan Chemical Co., Ltd.).

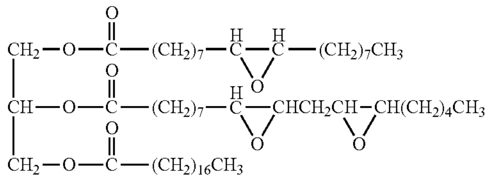

"Epoxy Compound 2": an epoxidized soy bean oil, molecular weight: 947, Newcizer 510R (manufactured by NOF Corporation).

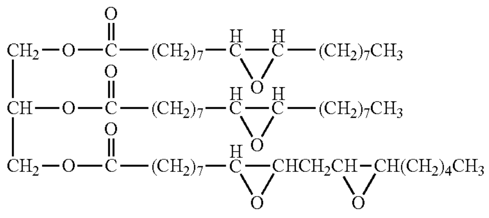

"Epoxy Compound 3": an epoxidized soy bean oil, Chemicizer SE-100 (manufactured by Sanwa Gouseikagaku Co., Ltd.).

"Epoxy Compound 4": an epoxidized linseed oil, Adekacizer O-180A (manufactured by Adeka Corporation).

"Epoxy Compound 5": an epoxidized rice bran oil $((C_{17}H_{33}OCO)_3O_3C_3H_5)$, molecular weight: 933, Chemicizer SE-80 (manufactured by Sanwa Gouseikagaku Co., Ltd.).

"Epoxy Compound 6": an epoxidized fatty acid ester represented by the following formula, molecular weight: 411, SANSO CIZER E-6000 (manufactured by New Japan Chemical Co., Ltd.).

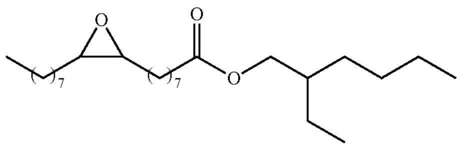

"Epoxy Compound 7": an epoxidized alicyclic carboxylic acid ester represented by the following formula, molecular weight: 411, SANSO CIZER E-PS (manufactured by New Japan Chemical Co., Ltd.).

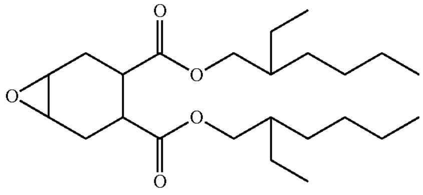 [SMILES: CCCCC(CC)COC(=O)C1CC2OC2CC1C(=O)OCC(CC)CCCC]

"Epoxy Compound 8": an epoxidized fatty acid ester $(C_{17}H_{33}OCOOC_8H_{17})$, molecular weight: 411, Chemicizer T-5000 (manufactured by Sanwa Gouseikagaku Co., Ltd.).

"Epoxy Compound 9": an epoxidized fatty acid ester $(C_{22}H_{42}O_3)$, molecular weight: 355, Chemicizer T-3000N (manufactured by Sanwa Gouseikagaku Co., Ltd.).

"Epoxy Compound 10": an epoxidized fatty acid ester $(C_{22}H_{44}O_4)$, molecular weight: 371, Chemicizer LE-3000 (manufactured by Sanwa Gouseikagaku Co., Ltd.).

"Epoxy Compound 11": an epoxidized fatty acid ester $(C_{19}H_{36}O_3)$, molecular weight: 312, Chemicizer T-2000 (manufactured by Sanwa Gouseikagaku Co., Ltd.).

<Epoxidized α-Olefin>

"Epoxidized α-olefin 1": C12, C14 mixed epoxidized α-olefin.

"Epoxidized α-olefin 2": C16 epoxidized α-olefin.

<Glycidyl Ether Compound (C)>

As the glycidyl ether compound (C), 2-ethylhexyl glycidyl ether was used.

<Other Additives>

Antioxidant: di-tert-butyl-p-cresol (DBPC).

Stabilizer: β-pinene.

Others: extreme pressure agent (tricresyl phosphate), silicone-based anti-foaming agent.

EXAMPLES 1 TO 34 AND COMPARATIVE EXAMPLES 1 TO 16

Each of the above components was mixed to prepare a refrigerator oil composition having a composition shown in Tables 1 to 3, and an autoclave test described below was performed.

The numerical unit of the blending composition in Tables 1 to 3 is "% by mass".

<Autoclave Test>

Autoclave test was performed in accordance with JIS K 2211:2009, Annex C. To be specific, a refrigerator oil mixture composition (moisture content: 2,000 ppm) obtained by mixing 30 g of the refrigerator oil composition of Examples 1 to 34 and Comparative Examples 1 to 16 and 30 g of R1234 yf, and a metal catalyst composed of iron, copper, and aluminum were housed in an autoclave having an internal volume of 200 mL. Next, after vacuuming was performed, the mixture was held at a temperature of 175° C. for 336 hours, and then an oil appearance and a catalyst appearance (presence or absence of deterioration) and the presence or absence of deposits (if there are deposits, the color thereof) were visually observed.

The oil appearance was evaluated by ASTM color, and those judged to be 0.5 or less (L0.5) were judged to have good oil appearance, and those judged to be greater than 0.5 (L1.0, L1.5, etc.) were judged to have poor oil appearance. Further, the acid value of the refrigerator oil composition and the fluorine amount in the refrigerator oil composition were evaluated by the methods described below.

(Evaluation of Acid Value of Refrigerator Oil Composition)

According to JIS K 2501:2003, it was measured by the indicator photometric titration method (refer to Appendix 1 in the above-mentioned JIS standard).

(Evaluation of Fluorine Amount in Refrigerator Oil Composition)

The fluorine amount in the refrigerator oil composition was measured by separating the refrigerant from the refrigerator oil mixture composition after the autoclave test and detecting fluorine ions (F) in the refrigerator oil composition in accordance with JIS K 0127:2013 (General Rules for Ion Chromatography Analysis).

TABLE 1

| | | | | Comparative Example | | | | | Example | |
|---|---|---|---|---|---|---|---|---|---|---|
| | | | Unit | 1 | 2 | 3 | 4 | 5 | 1 | 2 |
| Refrigerator oil composition | Base oil (A) | PVE1 | % by mass | 95.20 | 94.20 | 92.20 | 94.20 | 92.20 | 94.70 | 93.70 |
| | | PVE2 | % by mass | — | — | — | — | — | — | — |
| | | PAG | % by mass | — | — | — | — | — | — | — |
| | | ECP | % by mass | — | — | — | — | — | — | — |
| | | POE | % by mass | — | — | — | — | — | — | — |
| | Epoxy compound (B) | Epoxy compound 1 | % by mass | — | — | — | — | — | 0.50 | 1.50 |
| | | Epoxy compound 2 | % by mass | — | — | — | — | — | — | — |
| | | Epoxy compound 3 | % by mass | — | — | — | — | — | — | — |
| | | Epoxy compound 4 | % by mass | — | — | — | — | — | — | — |
| | | Epoxy compound 5 | % by mass | — | — | — | — | — | — | — |
| | | Epoxy compound 6 | % by mass | — | — | — | — | — | — | — |
| | | Epoxy compound 7 | % by mass | — | — | — | — | — | — | — |
| | | Epoxy compound 8 | % by mass | — | — | — | — | — | — | — |
| | | Epoxy compound 9 | % by mass | — | — | — | — | — | — | — |
| | | Epoxy compound 10 | % by mass | — | — | — | — | — | — | — |
| | | Epoxy compound 11 | % by mass | — | — | — | — | — | — | — |
| | Epoxidized α-olefin | Epoxidized α-olefin 1 | % by mass | — | 1.00 | 3.00 | — | — | — | — |
| | | Epoxidized α-olefin 2 | % by mass | — | — | — | 1.00 | 3.00 | — | — |
| | Glycidyl ether compound (C) | 2-ethylhexyl glycidyl ether | % by mass | 2.00 | 2.00 | 2.00 | 2.00 | 2.00 | 2.00 | 2.00 |
| | Antioxidant | DBPC | % by mass | 0.30 | 0.30 | 0.30 | 0.30 | 0.30 | 0.30 | 0.30 |
| | Stabilizer | β-pinene | % by mass | 1.40 | 1.40 | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 | 1.10 | 1.10 |
| | Total | | % by mass | 100.00 | 100.00 | 100.00 | 100.00 | 100.00 | 100.00 | 100.00 |
| | [(B)/(C)] (mass ratio) | | — | — | 0.00 | 0.00 | 0.00 | 0.00 | 0.25 | 0.75 |
| Test results | Oil appearance | | — | L0.5 | L0.5 | L0.5 | L0.5 | L0.5 | L0.5 | L0.5 |
| | Catalyst appearance | | — | ND* | ND* | ND* | ND* | ND* | ND* | ND* |
| | Acid value after autoclave test | | mgKOH/g | 0.25 | 0.23 | 0.20 | 0.26 | 0.23 | 0.18 | 0.13 |

TABLE 1-continued

| | | | | | | | | | |
|---|---|---|---|---|---|---|---|---|---|
| | Fluorine amount after autoclave test | mass ppm | 25 | 22 | 20 | 31 | 21 | 19 | 12 |
| | Deposits | — | none | none | none | none | none | none | none |

| | | | Unit | Example 3 | Example 4 | Example 5 | Example 6 | Example 7 |
|---|---|---|---|---|---|---|---|---|
| Refrigerator oil composition | Base oil (A) | PVE1 | % by mass | 92.20 | 90.70 | 93.70 | 92.20 | 90.70 |
| | | PVE2 | % by mass | — | — | — | — | — |
| | | PAG | % by mass | — | — | — | — | — |
| | | ECP | % by mass | — | — | — | — | — |
| | | POE | % by mass | — | — | — | — | — |
| | Epoxy compound (B) | Epoxy compound 1 | % by mass | 3.00 | 4.50 | — | — | — |
| | | Epoxy compound 2 | % by mass | — | — | 1.50 | 3.00 | 4.50 |
| | | Epoxy compound 3 | % by mass | — | — | — | — | — |
| | | Epoxy compound 4 | % by mass | — | — | — | — | — |
| | | Epoxy compound 5 | % by mass | — | — | — | — | — |
| | | Epoxy compound 6 | % by mass | — | — | — | — | — |
| | | Epoxy compound 7 | % by mass | — | — | — | — | — |
| | | Epoxy compound 8 | % by mass | — | — | — | — | — |
| | | Epoxy compound 9 | % by mass | — | — | — | — | — |
| | | Epoxy compound 10 | % by mass | — | — | — | — | — |
| | | Epoxy compound 11 | % by mass | — | — | — | — | — |
| | Epoxidized α-olefin | Epoxidized α-olefin 1 | % by mass | — | — | — | — | — |
| | | Epoxidized α-olefin 2 | % by mass | — | — | — | — | — |
| | Glycidyl ether compound (C) | 2-ethylhexyl glycidyl ether | % by mass | 2.00 | 2.00 | 2.00 | 2.00 | 2.00 |
| | Antioxidant | DBPC | % by mass | 0.30 | 0.30 | 0.30 | 0.30 | 0.30 |
| | Stabilizer | β-pinene | % by mass | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 |
| | Total | | % by mass | 100.00 | 100.00 | 100.00 | 100.00 | 100.00 |
| | [(B)/(C)] (mass ratio) | | — | 1.50 | 2.25 | 0.75 | 1.50 | 2.25 |
| Test results | Oil appearance | | — | L0.5 | L0.5 | L0.5 | L0.5 | L0.5 |
| | Catalyst appearance | | — | ND* | ND* | ND* | ND* | ND* |
| | Acid value after autoclave test | | mgKOH/g | 0.11 | 0.08 | 0.13 | 0.12 | 0.09 |
| | Fluorine amount after autoclave test | | mass ppm | 8 | 3 | 9 | 8 | 5 |
| | Deposits | | — | none | none | none | none | none |

| | | | Unit | Example 8 | Example 9 | Example 10 | Example 11 | Example 12 | Example 13 |
|---|---|---|---|---|---|---|---|---|---|
| Refrigerator oil composition | Base oil (A) | PVE1 | % by mass | 92.20 | 92.20 | 94.20 | 94.70 | 94.20 | 92.20 |
| | | PVE2 | % by mass | — | — | — | — | — | — |
| | | PAG | % by mass | — | — | — | — | — | — |
| | | ECP | % by mass | — | — | — | — | — | — |
| | | POE | % by mass | — | — | — | — | — | — |
| | Epoxy compound (B) | Epoxy compound 1 | % by mass | — | — | — | — | — | — |
| | | Epoxy compound 2 | % by mass | — | — | — | — | — | — |
| | | Epoxy compound 3 | % by mass | 3.00 | — | — | — | — | — |
| | | Epoxy compound 4 | % by mass | — | 3.00 | — | — | — | — |
| | | Epoxy compound 5 | % by mass | — | — | 1.00 | — | — | — |
| | | Epoxy compound 6 | % by mass | — | — | — | 0.50 | 1.00 | 3.00 |
| | | Epoxy compound 7 | % by mass | — | — | — | — | — | — |
| | | Epoxy compound 8 | % by mass | — | — | — | — | — | — |
| | | Epoxy compound 9 | % by mass | — | — | — | — | — | — |
| | | Epoxy compound 10 | % by mass | — | — | — | — | — | — |
| | | Epoxy compound 11 | % by mass | — | — | — | — | — | — |
| | Epoxidized α-olefin | Epoxidized α-olefin 1 | % by mass | — | — | — | — | — | — |
| | | Epoxidized α-olefin 2 | % by mass | — | — | — | — | — | — |

TABLE 1-continued

| | | | | | | | | | |
|---|---|---|---|---|---|---|---|---|---|
| | Glycidyl ether compound (C) | 2-ethylhexyl glycidyl ether | % by mass | 2.00 | 2.00 | 2.00 | 2.00 | 2.00 | 2.00 |
| | Antioxidant | DBPC | % by mass | 0.30 | 0.30 | 0.30 | 0.30 | 0.30 | 0.30 |
| | Stabilizer | β-pinene | % by mass | 1.40 | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 | 1.10 |
| | Total | | % by mass | 100.00 | 100.00 | 100.00 | 100.00 | 100.00 | 100.00 |
| | [(B)/(C)] (mass ratio) | | — | 1.50 | 1.50 | 0.50 | 0.25 | 0.50 | 1.50 |
| Test results | Oil appearance | | — | L0.5 | L0.5 | L0.5 | L0.5 | L0.5 | L0.5 |
| | Catalyst appearance | | — | ND* | ND* | ND* | ND* | ND* | ND* |
| | Acid value after autoclave test | | mgKOH/g | 0.11 | 0.12 | 0.15 | 0.09 | 0.11 | 0.13 |
| | Fluorine amount after autoclave test | | mass ppm | 10 | 8 | 9 | 15 | 7 | 11 |
| | Deposits | | — | none | none | none | none | none | none |

| | | | | Example | | | | |
|---|---|---|---|---|---|---|---|---|
| | | | Unit | 14 | 15 | 16 | 17 | 18 |
| Refrigerator oil composition | Base oil (A) | PVE1 | % by mass | 92.20 | 94.20 | 94.20 | 94.20 | 94.20 |
| | | PVE2 | % by mass | — | — | — | — | — |
| | | PAG | % by mass | — | — | — | — | — |
| | | ECP | % by mass | — | — | — | — | — |
| | | POE | % by mass | — | — | — | — | — |
| | Epoxy compound (B) | Epoxy compound 1 | % by mass | — | — | — | — | — |
| | | Epoxy compound 2 | % by mass | — | — | — | — | — |
| | | Epoxy compound 3 | % by mass | — | — | — | — | — |
| | | Epoxy compound 4 | % by mass | — | — | — | — | — |
| | | Epoxy compound 5 | % by mass | — | — | — | — | — |
| | | Epoxy compound 6 | % by mass | — | — | — | — | — |
| | | Epoxy compound 7 | % by mass | 3.00 | — | — | — | — |
| | | Epoxy compound 8 | % by mass | — | 1.00 | — | — | — |
| | | Epoxy compound 9 | % by mass | — | — | 1.00 | — | — |
| | | Epoxy compound 10 | % by mass | — | — | — | 1.00 | — |
| | | Epoxy compound 11 | % by mass | — | — | — | — | 1.00 |
| | Epoxidized α-olefin | Epoxidized α-olefin 1 | % by mass | — | — | — | — | — |
| | | Epoxidized α-olefin 2 | % by mass | — | — | — | — | — |
| | Glycidyl ether compound (C) | 2-ethylhexyl glycidyl ether | % by mass | 2.00 | 2.00 | 2.00 | 2.00 | 2.00 |
| | Antioxidant | DBPC | % by mass | 0.30 | 0.30 | 0.30 | 0.30 | 0.30 |
| | Stabilizer | β-pinene | % by mass | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 |
| | Total | | % by mass | 100.00 | 100.00 | 100.00 | 100.00 | 100.00 |
| | [(B)/(C)] (mass ratio) | | — | 1.50 | 0.50 | 0.50 | 0.50 | 0.50 |
| Test results | Oil appearance | | — | L0.5 | L0.5 | L0.5 | L0.5 | L0.5 |
| | Catalyst appearance | | — | ND* | ND* | ND* | ND* | ND* |
| | Acid value after autoclave test | | mgKOH/g | 0.15 | 0.13 | 0.15 | 0.10 | 0.12 |
| | Fluorine amount after autoclave test | | mass ppm | 17 | 17 | 9 | 9 | 12 |
| | Deposits | | — | none | none | none | none | none |

ND*: No Discoloration

TABLE 2

| | | | Unit | Comparative Example 6 | Comparative Example 7 | Comparative Example 8 | Comparative Example 9 | Comparative Example 10 | Example 19 | Example 20 |
|---|---|---|---|---|---|---|---|---|---|---|
| Refrigerator oil composition | Base oil (A) | PVE1 | % by mass | — | — | — | — | — | — | — |
| | | PVE2 | % by mass | 95.20 | 94.20 | 92.20 | 94.20 | 92.20 | 94.70 | 92.20 |
| | | PAG | % by mass | — | — | — | — | — | — | — |
| | | ECP | % by mass | — | — | — | — | — | — | — |
| | | POE | % by mass | — | — | — | — | — | — | — |
| | Epoxy compound (B) | Epoxy compound 1 | % by mass | — | — | — | — | — | 0.50 | 3.00 |
| | | Epoxy compound 2 | % by mass | — | — | — | — | — | — | — |
| | | Epoxy compound 3 | % by mass | — | — | — | — | — | — | — |
| | | Epoxy compound 4 | % by mass | — | — | — | — | — | — | — |
| | | Epoxy compound 5 | % by mass | — | — | — | — | — | — | — |
| | | Epoxy compound 6 | % by mass | — | — | — | — | — | — | — |
| | | Epoxy compound 7 | % by mass | — | — | — | — | — | — | — |
| | | Epoxy compound 8 | % by mass | — | — | — | — | — | — | — |
| | | Epoxy compound 9 | % by mass | — | — | — | — | — | — | — |
| | | Epoxy compound 10 | % by mass | — | — | — | — | — | — | — |
| | | Epoxy compound 11 | % by mass | — | — | — | — | — | — | — |
| | Epoxidized α-olefin | Epoxidized α-olefin 1 | % by mass | — | 1.00 | 3.00 | — | — | — | — |
| | | Epoxidized α-olefin 2 | % by mass | — | — | — | 1.00 | 3.00 | — | — |
| | Glycidyl ether compound (C) | 2-ethylhexyl glycidyl ether | % by mass | 2.00 | 2.00 | 2.00 | 2.00 | 2.00 | 2.00 | 2.00 |
| | Antioxidant | DBPC | % by mass | 0.30 | 0.30 | 0.30 | 0.30 | 0.30 | 0.30 | 0.30 |
| | Stabilizer | β-pinene | % by mass | 1.40 | 1.40 | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 | 1.10 | 1.10 |
| | Total | | % by mass | 100.00 | 100.00 | 100.00 | 100.00 | 100.00 | 100.00 | 100.00 |
| | [(B)/(C)] (mass ratio) | | — | 0.00 | 0.00 | 0.00 | 0.00 | 0.00 | 0.25 | 1.50 |
| Test results | Oil appearance | | — | L0.5 | L0.5 | L0.5 | L0.5 | L0.5 | L0.5 | L0.5 |
| | Catalyst appearance | | — | ND* | ND* | ND* | ND* | ND* | ND* | ND* |
| | Acid value after autoclave test | | mgKOH/g | 0.27 | 0.30 | 0.24 | 0.35 | 0.33 | 0.19 | 0.10 |
| | Fluorine amount after autoclave test | | mass ppm | 23 | 28 | 22 | 28 | 25 | 18 | 9 |
| | Deposits | | — | none | none | none | none | none | none | none |

| | | | Unit | Example 21 | Example 22 | Example 23 | Example 24 | Example 25 | Example 26 |
|---|---|---|---|---|---|---|---|---|---|
| Refrigerator oil composition | Base oil (A) | PVE1 | % by mass | — | — | — | — | — | — |
| | | PVE2 | % by mass | 92.20 | 92.20 | 94.20 | 94.70 | 94.20 | 94.20 |
| | | PAG | % by mass | — | — | — | — | — | — |
| | | ECP | % by mass | — | — | — | — | — | — |
| | | POE | % by mass | — | — | — | — | — | — |
| | Epoxy compound (B) | Epoxy compound 1 | % by mass | — | — | — | — | — | — |
| | | Epoxy compound 2 | % by mass | 3.00 | — | — | — | — | — |
| | | Epoxy compound 3 | % by mass | — | — | — | — | — | — |
| | | Epoxy compound 4 | % by mass | — | 3.00 | — | — | — | — |
| | | Epoxy compound 5 | % by mass | — | — | 1.00 | — | — | — |
| | | Epoxy compound 6 | % by mass | — | — | — | 0.50 | 1.00 | — |
| | | Epoxy compound 7 | % by mass | — | — | — | — | — | — |
| | | Epoxy compound 8 | % by mass | — | — | — | — | — | 1.00 |
| | | Epoxy compound 9 | % by mass | — | — | — | — | — | — |
| | | Epoxy compound 10 | % by mass | — | — | — | — | — | — |
| | | Epoxy compound 11 | % by mass | — | — | — | — | — | — |
| | Epoxidized α-olefin | Epoxidized α-olefin 1 | % by mass | — | — | — | — | — | — |
| | | Epoxidized α-olefin 2 | % by mass | — | — | — | — | — | — |
| | Glycidyl ether compound (C) | 2-ethylhexyl glycidyl ether | % by mass | 2.00 | 2.00 | 2.00 | 2.00 | 2.00 | 2.00 |

TABLE 2-continued

| | | | | | | | | | |
|---|---|---|---|---|---|---|---|---|---|
| | Antioxidant | DBPC | % by mass | 0.30 | 0.30 | 0.30 | 0.30 | 0.30 | 0.30 |
| | Stabilizer | β-pinene | % by mass | 1.40 | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 | 1.10 |
| | Total | | % by mass | 100.00 | 100.00 | 100.00 | 100.00 | 100.00 | 100.00 |
| | [(B)/(C)] (mass ratio) | | — | 1.50 | 1.50 | 0.50 | 0.25 | 0.50 | 0.50 |
| Test results | Oil appearance | | — | L0.5 | L0.5 | L0.5 | L0.5 | L0.5 | L0.5 |
| | Catalyst appearance | | — | ND* | ND* | ND* | ND* | ND* | ND* |
| | Acid value after autoclave test | | mgKOH/g | 0.14 | 0.15 | 0.13 | 0.08 | 0.09 | 0.13 |
| | Fluorine amount after autoclave test | | mass ppm | 10 | 11 | 8 | 13 | 8 | 13 |
| | Deposits | | — | none | none | none | none | none | none |

ND*: No Discoloration

TABLE 3

| | | | | Comparative Example | | | | | | Example |
|---|---|---|---|---|---|---|---|---|---|---|
| | | | Unit | 11 | 12 | 13 | 14 | 15 | 16 | 27 |
| Refrigerator oil composition | Base oil (A) | PVE1 | % by mass | — | — | — | — | — | — | — |
| | | PVE2 | % by mass | — | — | — | — | — | — | — |
| | | PAG | % by mass | 95.20 | 94.20 | 92.20 | — | — | — | 94.70 |
| | | ECP | % by mass | — | — | — | 95.20 | 94.20 | 92.20 | — |
| | | POE | % by mass | — | — | — | — | — | — | — |
| | Epoxy compound (B) | Epoxy compound 1 | % by mass | — | — | — | — | — | — | 0.50 |
| | | Epoxy compound 2 | % by mass | — | — | — | — | — | — | — |
| | | Epoxy compound 3 | % by mass | — | — | — | — | — | — | — |
| | | Epoxy compound 4 | % by mass | — | — | — | — | — | — | — |
| | | Epoxy compound 5 | % by mass | — | — | — | — | — | — | — |
| | | Epoxy compound 6 | % by mass | — | — | — | — | — | — | — |
| | | Epoxy compound 7 | % by mass | — | — | — | — | — | — | — |
| | | Epoxy compound 8 | % by mass | — | — | — | — | — | — | — |
| | | Epoxy compound 9 | % by mass | — | — | — | — | — | — | — |
| | | Epoxy compound 10 | % by mass | — | — | — | — | — | — | — |
| | | Epoxy compound 11 | % by mass | — | — | — | — | — | — | — |
| | Epoxidized α-olefin | Epoxidized α-olefin 1 | % by mass | — | 1.00 | 3.00 | — | — | — | — |
| | | Epoxidized α-olefin 2 | % by mass | — | — | — | — | 1.00 | 3.00 | — |
| | Glycidyl ether compound (C) | 2-ethylhexyl glycidyl ether | % by mass | 2.00 | 2.00 | 2.00 | 2.00 | 2.00 | 2.00 | 2.00 |
| | Antioxidant | DBPC | % by mass | 0.30 | 0.30 | 0.30 | 0.30 | 0.30 | 0.30 | 0.30 |
| | Stabilizer | β-pinene | % by mass | 1.40 | 1.40 | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 | 1.10 | 1.10 |
| | Total | | % by mass | 100.0 | 100.0 | 100.0 | 100.0 | 100.0 | 100.0 | 100.0 |
| | [(B)/(C)] (mass ratio) | | — | 0.00 | 0.00 | 0.00 | 0.00 | 0.00 | 0.00 | 0.25 |
| Test results | Oil appearance | | — | L0.5 | L0.5 | L0.5 | L0.5 | L0.5 | L0.5 | L0.5 |
| | Catalyst appearance | | — | ND* | ND* | ND* | ND* | ND* | ND* | ND* |
| | Acid value after autoclave test | | mgKOH/g | 0.20 | 0.22 | 0.20 | 0.26 | 0.27 | 0.24 | 0.16 |
| | Fluorine amount after autoclave test | | mass ppm | 23 | 24 | 21 | 31 | 35 | 28 | 15 |
| | Deposits | | — | none | none | none | none | none | none | none |

| | | | | Example | | | | | | |
|---|---|---|---|---|---|---|---|---|---|---|
| | | | Unit | 28 | 29 | 30 | 31 | 32 | 33 | 34 |
| Refrigerator oil composition | Base oil (A) | PVE1 | % by mass | — | — | — | — | — | — | — |
| | | PVE2 | % by mass | — | — | — | — | — | — | — |
| | | PAG | % by mass | — | — | 92.20 | 94.70 | — | — | 94.20 |
| | | ECP | % by mass | 94.70 | — | — | — | 94.70 | — | — |
| | | POE | % by mass | — | 94.70 | — | — | — | 94.70 | — |
| | Epoxy compound (B) | Epoxy compound 1 | % by mass | 0.50 | 0.50 | 3.00 | — | — | — | — |
| | | Epoxy compound 2 | % by mass | — | — | — | — | — | — | — |
| | | Epoxy compound 3 | % by mass | — | — | — | — | — | — | — |
| | | Epoxy compound 4 | % by mass | — | — | — | — | — | — | — |

TABLE 3-continued

| | | | | | | | | | | |
|---|---|---|---|---|---|---|---|---|---|---|
| | | Epoxy compound 5 | % by mass | — | — | — | — | — | — | — |
| | | Epoxy compound 6 | % by mass | — | — | — | 0.50 | 0.50 | 0.50 | 1.00 |
| | | Epoxy compound 7 | % by mass | — | — | — | — | — | — | — |
| | | Epoxy compound 8 | % by mass | — | — | — | — | — | — | — |
| | | Epoxy compound 9 | % by mass | — | — | — | — | — | — | — |
| | | Epoxy compound 10 | % by mass | — | — | — | — | — | — | — |
| | | Epoxy compound 11 | % by mass | — | — | — | — | — | — | — |
| | Epoxidized α-olefin | Epoxidized α-olefin 1 | % by mass | — | — | — | — | — | — | — |
| | | Epoxidized α-olefin 2 | % by mass | — | — | — | — | — | — | — |
| | Glycidyl ether compound (C) | 2-ethylhexyl glycidyl ether | % by mass | 2.00 | 2.00 | 2.00 | 2.00 | 2.00 | 2.00 | 2.00 |
| | Antioxidant | DBPC | % by mass | 0.30 | 0.30 | 0.30 | 0.30 | 0.30 | 0.30 | 0.30 |
| | Stabilizer | β-pinene | % by mass | 1.40 | 1.40 | 1.40 | 1.40 | 1.40 | 1.40 | 1.40 |
| | Others | Extreme pressure agent, Silicone-based anti-foaming agent | % by mass | 1.10 | 1.10 | 1.10 | 1.10 | 1.10 | 1.10 | 1.10 |
| | Total | | % by mass | 100.0 | 100.0 | 100.0 | 100.0 | 100.0 | 100.0 | 100.0 |
| | [(B)/(C)] (mass ratio) | | — | 0.25 | 0.25 | 1.50 | 0.25 | 0.25 | 0.25 | 0.50 |
| Test results | Oil appearance | | — | L0.5 | L0.5 | L0.5 | L0.5 | L0.5 | L0.5 | L0.5 |
| | Catalyst appearance | | — | ND* | ND* | ND* | ND* | ND* | ND* | ND* |
| | Acid value after autoclave test | | mgKOH/g | 0.17 | 0.19 | 0.08 | 0.06 | 0.05 | 0.09 | 0.05 |
| | Fluorine amount after autoclave test | | mass ppm | 18 | 16 | 7 | 11 | 9 | 14 | 5 |
| | Deposits | | — | none | none | none | none | none | none | none |

ND*: No Discoloration

The following can be seen from Tables 1 to 3.

It can be seen that the refrigerator oil composition of Examples 1 to 34 containing the epoxy compound (B) has an excellent effect of suppressing an increase in the acid value of the refrigerator oil composition after the autoclave test, and the fluorine amount in the refrigerator oil composition after the test is also small.

In particular, it can be seen that the refrigerator oil composition of Examples 3, 6, 9, 13, and 14 in which 3.00% by mass of the epoxy compound (B) was blended had an extremely excellent effect of suppressing an increase in the acid value of the refrigerator oil composition after the autoclave test than the refrigerator oil composition of Comparative Example 3 in which the same amount (3.00% by mass) of the epoxidized α-olefin was blended, and the fluorine amount in the refrigerator oil composition after the test was also small.

From the above results, it is presumed that the epoxy compound (B) suppresses the decomposition of the refrigerant, captures fluorine (F) eluted into the refrigerator oil composition by the decomposition of the refrigerant, and suppresses the increase in the acid value of the refrigerator oil composition by the action of reducing the amount of fluorine (F.) in the refrigerator oil composition.

The invention claimed is:

1. A refrigerator oil mixture composition, comprising:

a refrigerant comprising at least one unsaturated fluorinated hydrocarbon compound of the following formula (1):

$$C_xF_yH_z \quad (1),$$

wherein x is an integer of 2 to 6, y is an integer of 1 to 11, z is an integer of 1 to 11, and one or more carbon-carbon unsaturated bonds are present;

a base oil (A) selected from the group consisting of a polyalkylene glycol compound, a polyvinyl ether compound, a copolymer of poly (oxy) alkylene glycol or a monoether thereof and a polyvinyl ether, and a polyol ester compound;

an epoxy compound (B), wherein the epoxy compound (B) comprises the following groups (B1) and (B2), and a glycidyl ether compound (C);

(B1) at least one divalent group represented by the following formula (1);

(1)

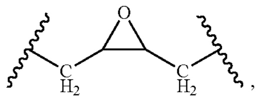

(B2) at least one ester group, wherein the epoxy compound (B) is at least one selected from the group consisting of an epoxidized fatty acid ester represented by the following general formula (1-1), an epoxidized alicyclic carboxylic acid ester represented by the following general formula (1-2), and an epoxidized vegetable oil:

(1-1)

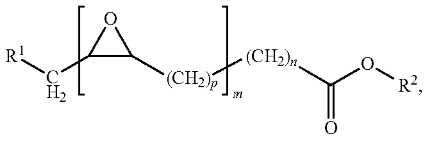

wherein $R^1$ is a hydrocarbon group having 4 to 20 carbon atoms, $R^2$ is a hydrocarbon group having 1 to 10 carbon atoms, p is an integer of 1 to 3, n is an integer of 0 to 12, m is an integer of 1 to 3, and when m is 2 or more, a plurality of structures in brackets [] may be the same as or different from each other, and (1-2)

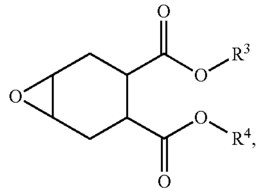

wherein $R^3$ and $R^4$ are each independently a hydrocarbon group having 4 to 20 carbon atoms, wherein the epoxidized vegetable oil is at least one selected from the group consisting of an epoxidized soybean oil, an epoxidized linseed oil, an epoxidized rice bran oil, and an epoxidized cottonseed oil, wherein a content of the epoxy compound (B) is from 0.10% by mass to 10.00% by mass based on the total amount of the refrigerator oil composition, and wherein a content of the glycidyl ether compound (C) is from 0.10 to 10.00% by mass based on the total amount of the refrigerator oil composition.

2. The refrigerator oil mixture composition according to claim 1, wherein the epoxy compound (B) has a molecular weight of at least 300.

3. The refrigerator oil mixture composition according to claim 1, wherein a content ratio [(B)/(C)] of the epoxy compound (B) to the glycidyl ether compound (C) is from 0.050 to 5.0 in terms of mass ratio.

4. The refrigerator oil mixture composition according to claim 1, further comprising at least one additive selected from the group consisting of an antioxidant, a stabilizer, an extreme pressure agent, and an anti-foaming agent.

5. The refrigerator oil mixture composition according to claim 1, wherein the unsaturated fluorinated hydrocarbon compound comprises at least one selected from the group consisting of R1234ze, R1234yf, and R1234ye.

6. The refrigerator oil mixture composition according to claim 1, wherein the refrigerant consists only of the unsaturated fluorinated hydrocarbon compound.

7. A method for producing a refrigerator oil composition, comprising at least one unsaturated fluorinated hydrocarbon compounds selected from compounds represented by the following formula (1):

$$C_xF_yH_z \quad (1),$$

wherein x is an integer of 2 to 6, y is an integer of 1 to 11, z is an integer of 1 to 11, and one or more carbon-carbon unsaturated bonds are present, the method comprising mixing a base oil (A) selected from the group consisting of a polyalkylene glycol compound, a polyvinyl ether compound, a copolymer of poly(oxy)alkylene glycol or a monoether thereof and a polyvinyl ether, and a polyol ester compound;

an epoxy compound (B), wherein the epoxy compound (B) comprises the following groups (B1) and (B2), and a glycidyl ether compound (C);

(B1) at least one divalent group represented by the following formula (1);

(1)

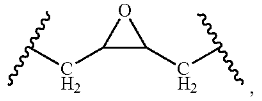

(B2) at least one ester group, wherein the epoxy compound (B) is at least one selected from the group consisting of an epoxidized fatty acid ester represented by the following general formula (1-1), an epoxidized alicyclic carboxylic acid ester represented by the following general formula (1-2), and an epoxidized vegetable oil:

(1-1)

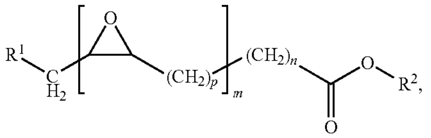

wherein $R^1$ is a hydrocarbon group having 4 to 20 carbon atoms, $R^2$ is a hydrocarbon group having 1 to 10 carbon atoms, p is an integer of 1 to 3, n is an integer of 0 to 12, m is an integer of 1 to 3, and when m is 2 or more, a plurality of structures in brackets [] may be the same as or different from each other, and (1-2)

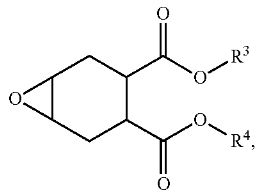

wherein $R^3$ and $R^4$ are each independently a hydrocarbon group having 4 to 20 carbon atoms, wherein the epoxidized vegetable oil is at least one selected from the group consisting of an epoxidized soybean oil, an epoxidized linseed oil, an epoxidized rice bran oil, and an epoxidized cottonseed oil, wherein a content of the epoxy compound (B) is from 0.10% by mass to 10.00% by mass based on the total amount of the refrigerator oil composition, and wherein a content of the glycidyl ether compound (C) is from 0.10 to 10.00% by mass based on the total amount of the refrigerator oil composition.

* * * * *